United States Patent [19]

Burns et al.

[11] Patent Number: 4,861,701
[45] Date of Patent: Aug. 29, 1989

[54] PHOTOGRAPHIC ELEMENT AND PROCESS COMPRISING A COMPOUND WHICH COMPRISES TWO TIMING GROUPS IN SEQUENCE

[75] Inventors: Paul A. Burns; Terry R. Taber, both of Rochester, N.Y.

[73] Assignee: Eastman Kodak Company, Rochester, N.Y.

[21] Appl. No.: 105,062

[22] Filed: Oct. 5, 1987

Related U.S. Application Data

[63] Continuation of Ser. 890,674, Jul. 30, 1986, abandoned.

[51] Int. Cl.$^4$ .................................................. G03C 7/32
[52] U.S. Cl. ...................................... 430/543; 430/544; 430/553; 430/555; 430/557; 430/564; 430/566; 430/955; 430/957; 430/958; 430/959
[58] Field of Search ............... 430/543, 544, 553, 555, 430/557, 566, 564, 955, 957, 958, 959

[56] References Cited

U.S. PATENT DOCUMENTS

| | | | |
|---|---|---|---|
| 4,248,962 | 2/1981 | Lau ........................................ | 430/382 |
| 4,310,618 | 1/1982 | Fernandez et al. .................. | 430/381 |
| 4,409,323 | 10/1983 | Sato et al. ........................... | 430/544 |
| 4,468,450 | 9/1984 | Meneghini et al. ................. | 430/222 |
| 4,477,563 | 10/1984 | Ichijima et al. ..................... | 430/544 |

FOREIGN PATENT DOCUMENTS 085580 10/1983 European Pat. Off. .
57-56837 4/1982 Japan .
60-225156 11/1985 Japan .
61-156127 7/1986 Japan .

OTHER PUBLICATIONS

Research Disclosure, Dec. 1978, Item No. 17643.
Research Disclosure, Jan. 1983, Item No. 22534.

Primary Examiner—Paul R. Michl
Assistant Examiner—Patrick A. Doody
Attorney, Agent, or Firm—Richard E. Knapp

[57] ABSTRACT

Photographic compounds capable of releasing a photographically useful group are more effective in photographic materials when the photographic compounds comprise at least two differing timing groups in sequence between a carrier moiety and the photographically useful group. The two timing groups in sequence enable improved timing and control of release of the photographically useful group.

16 Claims, No Drawings

PHOTOGRAPHIC ELEMENT AND PROCESS COMPRISING A COMPOUND WHICH COMPRISES TWO TIMING GROUPS IN SEQUENCE

This is a continuation of application Serial No. 890,674, filed July 30, 1986, now abandoned.

BACKGROUND OF THE INVENTION

1. Field of the Invention

This invention relates to new photographic compounds which release photographically useful groups during photographic processing and to photographic materials and processes using such compounds.

2. Description of the State of the Art

Various ways are recognized in the photographic art for release of a photographically useful group (PUG) from a compound, such as a coupler, in photographic materials and processes. For example, U.S. Pat. No. 4,248,962, describes compounds that release a photographically useful group by means of an intramolecular nucleophilic displacement reaction in photographic materials. Other examples are described in U.S. Pat. No. 4,409,323, wherein couplers are described which release a photographically useful group by means of an electron transfer down a conjugated chain. These compounds capable of releasing a photographically useful group in a photographic material upon processing provide a degree of control over the timing and rate of release as well as the rate of diffusion and distance of diffusion of the photographically useful group in the photographic material.

A need has continued to exist for a higher degree of control over these parameters as well as a higher degree of freedom in the capability to design compounds having releasable photographically useful groups. Moreover, such needs have existed with the added parameter that such compounds must not require significantly modifying the photographically useful groups or the carrier compounds, such as the couplers, from which the photographically useful group are released, in a way which would be inconsistent with the ultimate use for which each is intended.

SUMMARY OF THE INVENTION

The present invention solves these problems by means of a photographic element comprising a support, at least one photographic emulsion layer and at least one compound A capable of releasing a photographically useful group (PUG), wherein the compound A comprises at least two differing timing groups in sequence capable, upon activation, of timing the release of the PUG and wherein at least two separate fragments are formed from the two differing timing groups upon processing the photographic element. A preferred compound (A) in a photographic element is a coupler having two differing timing groups, $T_1$ and $T_2$, in sequence. The timing groups are each capable upon activation of timing the release of the PUG. Also, two separate differing fragments are formed from the two differing timing groups. A highly preferred compound (A) has in sequence a timing group ($T_1$) capable of an intramolecular nucleophilic displacement reaction to enable timed release and a timing group ($T_2$) capable of electron transfer down a conjugated chain to enable timed release.

One embodiment of the invention is the photographic element comprising compound A as described. Another embodiment is a process of forming a photographic image by developing an exposed photographic element by means of a color developing agent in the presence of a compound A, particularly a coupler, as described. A further embodiment is a new coupler represented by the structure:

$$\text{COUP}-(T_1)-(T_2)-\text{PUG}$$

wherein:
COUP is a coupler moiety;
$T_1$ is a first timing group capable of being released from COUP at the coupling position of COUP;
$T_2$ is a second timing group, different from $T_1$, capable of being released from $T_1$ after $T_1$ is released from COUP; and
PUG is a photographically useful group.

The compound A, preferably a coupler, contains two differing timing groups, in sequence capable upon activation of sequentially timing the release of a PUG. The reaction of compound A, preferably a coupler, with oxidized color developing agent cleaves the bond between the first timing group ($T_1$) and the carrier portion of compound A, preferably the coupler moiety (COUP). Then the bond between the first timing group ($T_1$) and the second timing group ($T_2$) is cleaved. Finally, the bond between the second timing group ($T_2$) and the PUG is cleaved enabling the PUG to perform its intended function. Bond cleavage between $T_1$ and $T_2$ or between $T_2$ and PUG preferably does not involve the action of oxidized color developer. The sequential cleavage of the bond between the carrier portion of compound A and the first timing group, then the bond between the first timing group ($T_1$) and the second timing group ($T_2$), and finally the bond between the PUG and the second timing group ($T_2$) enables the improved control over timing and rate of release of PUG. The sequential cleavage of these bonds is a characteristic feature of the invention.

One advantage of compounds of the invention is the greater variety of workable linking groups available for organic synthesis. Another advantage is that for the first time an extended timing period is available during which none of the PUG is released. For a given PUG, available single timing groups may provide a release rate too fast or too slow for the desired application, while two differing timing groups in sequence allows flexibility in attaining the desired release rate, typically with a half-life in the 0.1 to 60 second range, such as 15 seconds to 60 seconds. $T_1$ and $T_2$ are particularly useful when they have essentially matching timing of release.

For compounds, such as couplers, involving release of a development inhibitor group in a photographic element, a coupler according to the invention enables more control over image sharpness, granularity, and balanced color reproduction without deleterious effects on desired properties, such as photographic speed and sensitometric curve shape. For compounds, such as couplers, involving release of a bleach accelerator group in a photographic material, this improved control of timed release enables processing steps, such as color development, prior to bleaching to proceed to completion without interference from prematurely released bleach accelerator. In photographic elements, particularly photographic elements involving diffusion of compounds and/or fragments of compounds between layers, the controlled delayed release according to the invention enables larger diffusion paths of a released fragment before release of a PUG and enables improved control of interlayer interimage effects.

A particularly useful coupler of the invention is represented by the formula:

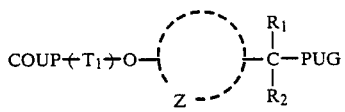

where COUP, $T_1$ and PUG are the same as described while Z represents atoms necessary to complete a substituted or unsubstituted pyridine, pyrazole, benzene or naphthalene nucleus and $R_1$ and $R_2$ individually represent a hydrogen atom, alkyl or aryl, with the group

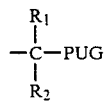

being joined to the nucleus at the para or ortho position relative to the oxygen atom.

In chemical systems requiring timed release of a moiety the release mechanisms can be initiated by any means that initiates cleavage of the first timing group from the carrier moiety. Depending on the particular carrier compound, the particular timing groups, and the desired end use of the active moiety, the release mechanism can be initiated by, for example, reaction of the carrier compound with radiation, enzymes, moisture, acid or base, and/or oxidized reducing agent.

As used herein the terms "coupler" and "coupler compound" refer to the entire compound, including the coupler moiety, the timing groups and the PUG, while the term "coupler moiety" refers to that portion of the compound other than the timing groups and the PUG.

The particular timing groups employed, including the linkage by which they are attached to other portions of coupler and the nature of the substituents on them, can be varied to help control such parameters as rate and time of cleavage of the timing groups and of the PUG. Since these parameters can be controlled by modification of the timing groups, they need not be emphasized in selecting the particular coupler moiety and the particular PUG, thus providing greater freedom in selecting such moieties and groups for a particular end use.

If the PUG is joined to the coupler moiety only through the timing groups, then cleavage of the bond between the first timing groups and the coupler moiety releases the timing groups and the PUG as a unit. In this embodiment the particular timing groups employed, including the nature of the substituents on them, can additionally control the rate and distance of diffusion of the unit formed by the timing groups and the PUG after this unit is released from the coupler moiety but before the PUG is released from the second timing group. If the PUG is joined to the coupler moiety both directly and through the timing groups, the particular timing groups and the nature of the substituents on them can control the rates of cleavage of the timing groups and can control the rate at which the PUG is released. In this embodiment the direct linkage between the PUG and the coupler moiety helps prevent diffusion of the PUG.

The coupler moiety can be any moiety which will react with oxidized color developing agent to cleave the bond between the first timing group and the coupler moiety. It includes coupler moieties employed in conventional color-forming couplers which yield colorless products on reaction with oxidized color developing agents as well as coupler moieties which yield colored products on reaction with oxidized color developing agents. Both types of coupler moieties are well known to those skilled in the art.

The coupler moiety can be unballasted or ballasted with an oil-soluble or fat-tail group. It can be monomeric, or it can form part of a dimeric, oligomeric or polymeric coupler, in which case more than one COUP+$T_1$)+$T_2$)-PUG group can be contained in the coupler, or it can form part of a bis compound in which the $T_1$, $T_2$ and/or PUG groups form part of the link between two coupler moieties.

It will be appreciated that, depending upon the particular coupler moiety, the particular color developing agent and the type of processing, the reaction product of the coupler moiety and oxidized color developing agent can be: (1) colored and nondiffusible, in which case it will remain in the location where it is formed; (2) colored and diffusible, in which case it may be removed during processing from the location where it is formed or allowed to migrate to a different location; or (3) colorless and diffusible or nondiffusible, in which case it will not contribute to image density. In cases (2) and (3) the reaction product may be initially colored and/or nondiffusible but converted to colorless and/or diffusible products during the course of processing.

The +$T_1$)+$T_2$)-PUG group is joined to the coupler moiety at any of the positions from which groups released from couplers by reaction with oxidized color developing agent can be attached. Preferably, the +$T_1$)+$T_2$)-PUG group is attached at the coupling position of the coupler moiety so that upon reaction of the coupler with oxidized color developing agent the +$T_1$)+$T_2$)-PUG group will be displaced. However, the +$T_1$)+$T_2$)-PUG group can be in a non-coupling position of the coupler moiety from which position it will be displaced as a result of reaction of the coupler with oxidized color developing agent. In the case where the +$T_1$)+$T_2$)-PUG group is in a non-coupling position of the coupler moiety, other groups can be in the coupling position, including conventional coupling-off groups or the same or a different PUG from that contained in the +$T_1$)+$T_2$)-PUG group. Alternatively, the coupler moiety can have a +$T_1$)+$T_2$)-PUG group in each of the coupling position and a non-coupling position. Accordingly, couplers of this invention can release more than one mole of PUG per mole of coupler. The PUGs can be the same or different and can be released at the same or different times and rates.

The first timing group ($T_1$) can be any organic group which will serve to connect COUP to the second timing group ($T_2$) and which, after cleavage from COUP will cleave from the second timing group ($T_2$), preferably by an intramolecular nucleophilic displacement reaction of the type described in, for example, U.S. Pat. No. 4,248,962.

As used herein, the term "intramolecular nucleophilic displacement reaction" refers to a reaction in which a nucleophilic center of a compound reacts directly, or indirectly through an intervening molecule, at another site on the compound, which is an electrophilic center, to effect displacement of a group or atom attached to the electrophilic center. Such compounds have a nucleophilic group and electrophilic group spatially related by the configuration of the molecule to promote reactive proximity. Preferably the nucleophilic group and the electrophilic group are located in the compound so that a cyclic organic ring, or a transient cyclic organic ring, can be easily formed by an intramolecular reaction involving the nucleophilic center and the electrophilic center.

A nucleophilic group is understood to be a grouping of atoms one of which is electron rich. This atom is referred to as the nucleophilic center. An electrophilic group is understood to be a grouping of atoms one of which is electron deficient. This atom is referred to as the electrophilic center.

Thus, in photographic couplers of this invention, the first timing group perferably contains a nucleophilic group and an electrophilic group which are spatially related with respect to one another so that upon release from the coupler moiety the nucleophilic center and the electrophilic center will react to effect displacement of the second timing group and PUG from the first timing group. In order to assure that the second timing group and the PUG are not released prior to release of the first timing group from the coupler moiety, the nucleophilic center should be prevented from reacting with the electrophilic center until such release and the electrophilic center should be resistant to external attack, e.g. hydrolysis. Premature reaction can be prevented by attaching the coupler moiety to the first timing group at the nucleophilic center or an atom in conjunction with a nucleophilic center, so that cleavage of the timing group and PUG from the coupler moiety unblocks the nucleophilic center and permits it to react with the electrophilic center, or by positioning the nucleophilic group and the electrophilic group so that they are prevented from coming into reactive proximity until release. Similarly, the second timing group will be attached at a position on the first timing group from which it will be displaced upon reaction of the nucleophilic center and the electrophilic center.

The second timing group ($T_2$) can be any organic group different from the first timing group ($T_1$), which will serve to connect the first timing group ($T_1$) to the PUG, and which, after cleavage from the first timing group ($T_1$), will cleave from the PUG. The cleavage of the second timing group ($T_2$) from the PUG is preferably by means of an electron transfer down a conjugated chain.

As used herein the term "electron transfer down a conjugated chain" is understood to refer to transfer of an electron along a chain of atoms in which alternate single bonds and double bonds occur. A conjugated chain is understood to have the same meaning as commonly used in organic chemistry. Electron transfer down a conjugated chain is as described in, for example, U.S. Pat. No. 4,409,323.

The timing groups ($T_1$ and/or $T_2$) can contain moieties and substituents which will permit control of (i) one or more of the rates of reaction of COUP with oxidized color developing agent, (ii) the rate of diffusion of $-(T_1)-(T_2)-PUG$ and/or $-(T_2)-PUG$ and (iii) the rate of release of PUG. The timing groups can contain additional substituents, such as additional PUGs, or precursors thereof, which may remain attached to the timing groups or be released.

The PUG can be any group that is desirably made available in a photographic element in an imagewise fashion. The PUG can be a photograhic dye or a photographic reagent. A photographic reagent herein is a moiety which upon release further reacts with components in the element, such as a development inhibitor, a development accelerator, a bleach inhibitor, a bleach accelerator, a coupler (e.g. a competing coupler, a color-forming coupler, a DIR coupler), a dye precursor, a dye, a developing agent (e.g. a competing developing agent, a dye-forming developing agent or a silver halide developing agent), a silver complexing agent, a fixing agent, an image toner, a stabilizer, a hardener, a tanning agent, a fogging agent, an ultraviolet radiation absorber, an antifoggant, a nucleator, a chemical or spectral sensitizer or a desensitizer. Such dyes and photographic reagents generally contain a hetero atom having a negative valence of 2 or 3 from Group VA or VIA of the Periodic Table, such as oxygen, sulfur, selenium and nitrogen (e.g., nitrogen in a heterocyclic ring). Such an atom can conveniently serve as the point on the dye or photographic reagent at which the second timing group ($T_2$) is joined.

The PUG can be present in the coupler as a preformed species or it can be present in a blocked form or as a precursor. For example, a preformed development inhibitor may be attached to the second timing group or the devlopment inhibiting function may be blocked by being the point of attachment to the second timing group. Other examples are (i) a preformed dye attached to the second timing group, (ii) a dye which is blocked so as to shift its spectral absorption attached to the second timing group, or (iii) a leuco dye attached to the second timing group.

Preferred compounds according to this invention are photographic couplers containing a coupler moiety, a PUG containing a hetero atom from Group VA or VIA of the Periodic Table having a negative valence of 2 or 3, and timing groups ($T_1$ and $T_2$) joining the coupler moiety and the PUG. The first timing group ($T_1$) perferably comprises a nucleophilic group attached to the coupler moiety at a position from which it is capable of being displaced as a result of reaction of the coupler moiety with oxidized color developing agent. The first timing group ($T_1$) also preferably comprises an electrophilic group attached to the second timing group ($T_2$) and capable of being displaced therefrom by the nucleophilic group after the nucleophilic group is displaced from the coupler moiety. The coupler also comprises a linking group spatially relating the nucleophilic group and the electrophilic group to enable an intramolecular nucleophilic displacement reaction which cleaves the bond between the second timing group ($T_2$) and the first timing group ($T_1$).

It will be appreciated that in the first timing group, for an intramolecular reaction to occur between the nucleophilic group and the electrophilic group, the groups should be spatially related after cleavage from the coupler, so that they can react with one another. Preferably, the nucleophilic group and the electrophilic group are spatially related within the first timing group so that the intramolecular nucleophilic displacement reaction involves the formation of a 3- to 7-membered ring, most preferably a 5- or 6-membered ring.

It will be further appreciated that for an intramolecular reaction to occur in the aqueous alkaline environment encountered during photograhic processing, displacing the second timing group from the first timing group, the thermodynamics should be such and the groups be so selected that the free energy of ring closure plus the bond energy of the bond formed between the nucleophilic group and the electrophilic group is greater than the bond energy between the electrophilic group and the second timing group. Not all possible combinations of nucleophilic group, linking group, electrophilic group and the atoms in the second timing group to which the electrophilic group is attached will yield a thermodynamic relationship favorable to breaking of the bond between the electrophilic group and the second timing group. However, it is within the skill of the art to select appropriate combinations taking the above energy relationships into account.

A preferred class of timing group ($T_1$) is represented by the structure:

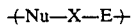

wherein:

Nu is a nucleophilic group attached to a position of COUP from which it will be displaced upon reaction of COUP with oxidized color developing agent;

E is an electrophilic group attached to an atom in the second timing group ($T_2$) and is displaceable therefrom by Nu after Nu is displaced from COUP; and X is a linking group for spatially relating Nu and E, upon displacement of Nu from COUP, to undergo an intramolecular nucleophilic displacement reaction with the formation of a 3- to 7-membered ring and thereby release ${+}T_2{+}$PUG.

Representative Nu groups contain electron rich oxygen, sulfur and nitrogen atoms. Representative E groups contain electron deficient carbonyl, thiocarbonyl, phosphonyl and thiophosphonyl moieties. Other useful Nu and E groups will be apparent to those skilled in the art.

In the following listings of representative Nu and E groups, the groups are oriented so that the lefthand bond of Nu is joined to COUP and the righthand bond of Nu is joined to X, while the lefthand bond of E is joined to X and the righthand bond of E is joined to ${+}T_2{+}$PUG.

Representative Nu groups include:

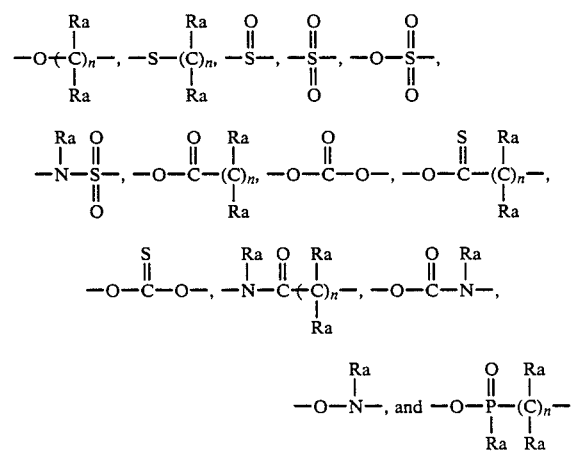

where each Ra is independently hydrogen, alkyl, such as alkyl of 1 to 20 carbon atoms including substituted alkyl such as methyl, ethyl, propyl, hexyl, decyl, pentadecyl, octadecyl, carboxyethyl, hydroxypropyl, sulfonamidobutyl and the like, or aryl, such as aryl of 6 to 20 carbon atoms including substituted aryl such as phenyl, naphthyl, benzyl, tolyl, t-butylphenyl, carboxyphenyl, chlorophenyl, hydroxyphenyl and the like, and n is an integer from 0 to 4 such that the ring formed by Nu, X and E upon nucleophilic attack of Nu upon the electrophilic center in E contains 3 to 7 ring atoms. Preferably Ra is hydrogen, lower alkyl of 1 to 4 carbon atoms or aryl of 6 to 10 carbon atoms.

Representative E groups include:

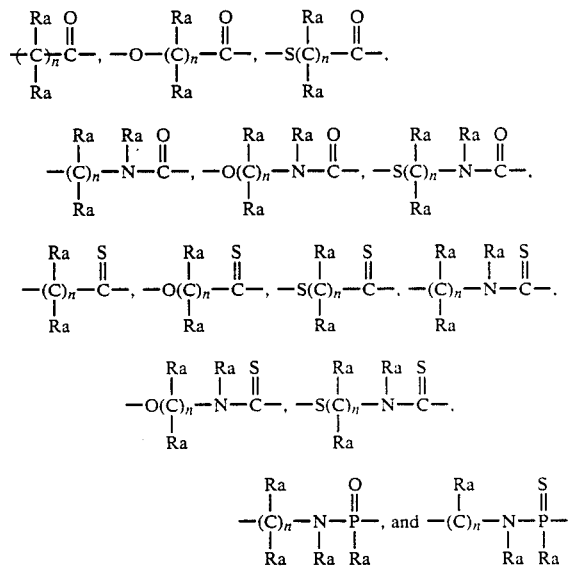

where Ra and n are as defined above.

E is preferably an electrophilic group selected from the group consisting of

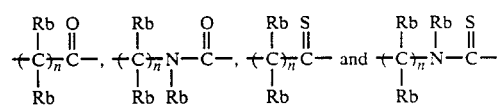

wherein each Rb is independently hydrogen, alkyl, such as alkyl containing 1 to 20 carbon atoms, preferably alkyl containing 1 to 4 carbon atoms, or aryl, such as aryl containing 6 to 20 carbon atoms, preferably aryl containing 6 to 10 carbon atoms; and n is 0 to 4, such that the ring formed upon reaction of the nucleophilic center in Nu with the electrophilic center in E contains 5- or 6-members.

The linking group represented by X can be an acyclic group such as alkylene, such as methylene, ethylene or propylene, or a cyclic group such as an aromatic group, such as phenylene or naphthylene, or a heterocyclic group, such as furan, thiophene, pyridine, quinoline or benzoxazine. Preferably X is alkylene or arylene. The groups Nu and E are attached to X to provide, upon release of Nu from COUP, favorable spatial relationship for nucleophilic attack of the nucleophilic center in Nu on the electrophilic center in E. When X is a cyclic group, Nu and E can be attached to the same or adjacent rings. Aromatic groups in which Nu and E are attached to adjacent ring positions are particularly preferred X groups.

X can be unsubstituted or substituted. The substituents can be those which will modify the rate of reaction, diffusion, or displacement, such as halogen, including fluoro, chloro, bromo, or iodo, nitro, alkyl of 1 to 20 carbon atoms, acyl, such as carboxy, carboxyalkyl, alkoxycarbonyl, alkoxycarbonamido, sulfoalkyl, alkyl-sulfonamido, and alkylsulfonyl, solubilizing groups, ballast groups and the like, or they can be substituents which are separately useful in the photographic element such as a stabilizer, an antifoggant, a dye (e.g., a filter dye, a solubilized masking dye) and the like. For example, solubilizing groups will increase the rate of diffusion; ballast groups will decrease the rate of diffusion; electron withdrawing groups will decrease the rate of displacement of the second timing group and PUGs which remain attached to X can serve functions such as stabilization, masking and the like.

There follows a listing of patents and publications which described representative COUP groups useful in the invention. Also listed are structures of preferred COUP, $T_1$, $T_2$, and PUG groups. In these structures Y represents, in the case of a dye forming coupler that is useful with couplers according to the invention, a hydrogen atom or a coupling-off group known in the photographic art. In the case of couplers according to the invention, Y represents $-(T_1)-(T_2)-PUG$ wherein $T_1$, $T_2$ and PUG are as defined above.

I. COUP's

A. Couplers which form cyan dyes upon reaction with oxidized color developing agents are described in such representative patents and publications as: U.S. Pat. Nos. 2,772,162, 2,895,826, 3,002,836, 3,034,892, 2,474,293, 2,423,730, 2,367,531, 3,041,236 and "Farbkuppler-eine Literaturübersicht," published in Agfa Mitteilungen, Band II, pp. 156-175 (1961).

Preferably such couplers are phenols and naphthols which form cyan dyes on reaction with oxidized color developing agent and have the $-(T_1)-(T_2)-PUG$ group attached to the coupling position, i.e. the carbon atom in the 4-position. Structures of preferred such coupler moieties are:

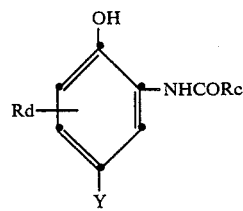

IA-1

IA-2

IA-3

IA-4 where Rc represents a ballast group, and Rd represents one or more halogen (e.g. chloro, fluoro), lower alkyl (e.g. methyl, ethyl, butyl) or lower alkoxy (e.g. methoxy, ethoxy, butoxy) groups.

B. Couplers which form magenta dyes upon reaction with oxidized color developing agent are described in such representative patents and publications as: U.S. Pat. Nos. 2,600,788, 2,369,489, 2,343,703, 2,311,082, 3,152,896, 3,519,429, 3,062,653, 2,908,573 and "Fabkupper-eine Literaturürubersicht," published in Agfa Mitteilungen, Band III, pp. 126-156 (1961).

Preferably, such couplers are pyrazolones and pyrazolotriazoles which form magenta dyes upon reaction with oxidized color developing agents and have the Y, i.e. $-(T_1)-(T_2)-PUG$ group, attached to the coupling position. Structures of preferred such coupler moieties are:

IB-1

IB-2

IB-3 where Rc and Rd are chosen independently to be a ballast group, alkyl, substituted alkyl, phenyl or substituted phenyl.

C. Couplers which form yellow dyes upon reaction with oxidized and color developing agent are described in such representative patents and publications as: U.S. Pat. Nos. 2,875,057, 2,407,210, 3,265,506, 2,298,443, 3,048,194, 3,447,928 and "Farbkuppler-eine Literatureü bersicht," published in Agfa Mitteilungen, Band III, pp. 112-126 (1961).

Preferably such yellow-dye forming couplers are acylacetamides, such as benzoylacetanilides and pivalylacetanilides, and have the $-(T_1)-(T_2)-PUG$ group attached to the coupling position, i.e. the active methylene carbon atom.

Structures of preferred such coupler moieties are:

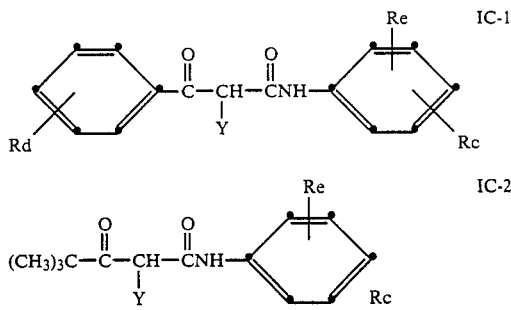

IC-1

IC-2

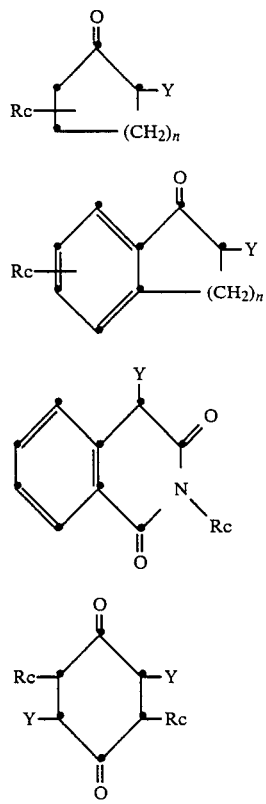

ID-1

ID-2

ID-3

ID-4 where Rc is as defined above and Rd and Re are hydrogen or one or more halogen, lower alkyl, such as methyl and ethyl, or ballast groups, such as alkoxy of 16 to 20 carbon atoms.

D. Couplers which form colorless products upon reaction with oxidized color developing agent are described in such representative patents as: U.K. Patent No. 861,138; U.S. Pat. Nos. 3,632,345, 3,928,041, 3,958,993 and 3,961,959. Preferably such couplers are cyclic carbonyl containing compounds which form colorless products on reaction with oxidized color developing agent and have the $\text{--}(T_1)\text{--}(T_2)\text{--}PUG$ group attached to the carbon atom in the $\alpha$-position with respect to the carbonyl group.

Structures of preferred such coupler moieties are:

where Rc is as defined above and n is 1 or 2.

E. Couplers which form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764.

Preferably such couplers are resorcinols or m-aminophenols which form black or neutral products on reaction with oxidized color developing agent and have the $\text{--}(T_1)\text{--}(T_2)\text{--}PUG$ group para to a hydroxy group.

Structures of preferred such coupler moieties are:

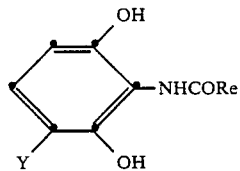

IE-1

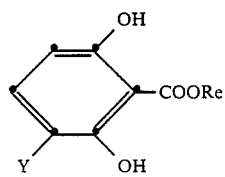

IE-2

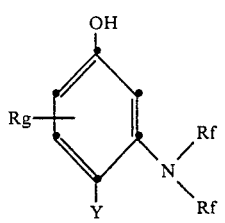

IE-3 where Re is alkyl of 3 to 20 carbon atoms, phenyl or phenyl substituted with hydroxy, halo, amino, alkyl of 1 to 20 carbon atoms or alkoxy of 1 to 20 carbon atoms; each Rf is independently hydrogen, alkyl of 1 to 20 carbon atoms, alkenyl of 1 to 20 carbon atoms, or aryl of 6 to 20 carbon atoms; and Rg is one or more halogen, alkyl of 1 to 20 carbon atoms, alkoxy of 1 to 20 carbon atoms or other monovalent organic groups.

II. First Timing Groups ($T_1$)

Examples of first timing groups ($T_1$) are as follows:

A. Acyclic $T_1$ groups:

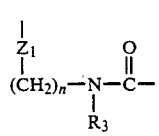

IIA-1 where n is 1-4, preferably 2 or 3, $Z_1$ is

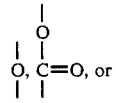

and $R_3$ is hydrogen, alkyl, such as alkyl of 1 to 20 carbon atoms, preferably lower alkyl of 1 to 4 carbon atoms, or aryl, such as aryl of 6 to 20 carbon atoms, preferably aryl of 6 to 10 carbon atoms.

B. Aromatic $T_1$ groups:

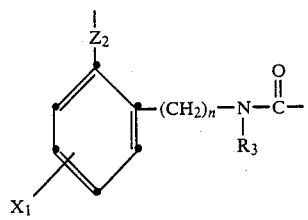

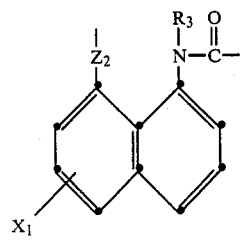

where n is 0 or 1; $Z_2$ is

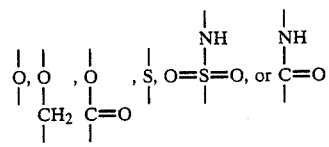

$R_3$ is as defined above; and $X_1$ is hydrogen or one or more substituent groups independently selected from cyano, fluoro, chloro, bromo, iodo, nitro, alkyl, such as alkyl of 1 to 20 carbon atoms, a dye, $-OR_4$, $-COOR_4$, $-CONHR_4$, $-NHCOR_4$, $NHSO_2R_4$, $-SO_2NHR_4$ of $SO_2R_4$, where $R_4$ is hydrogen, alkyl, such as alkyl of 1 to 20 carbon atoms, preferably alkyl of 1 to 4 carbon atoms, or aryl, such as aryl of 6 to 20 carbon atoms, preferably aryl of 6 to 10 carbon atoms.

C. Heterocyclic $T_1$ groups:

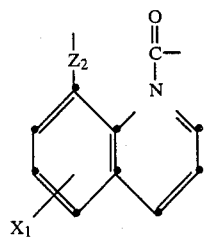

IIC-1

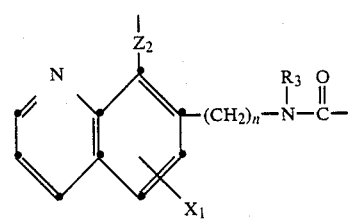

IIC-2

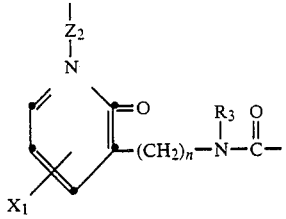

IIC-3 where n is 0 or 1, $Z_2$, $X_1$ and $R_3$ are as defined above.

D. Bis $T_1$ groups:

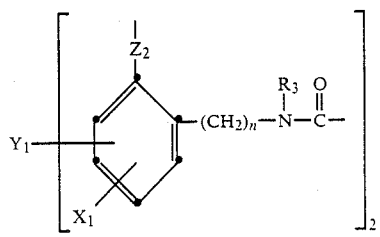

IID-1 where $Y_1$ is a linking group, such as

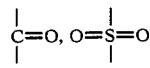

or $-NHSO_2CH_2SO_2NH-$; n is 0 or 1 and $X_1$, $Z_2$ and $R_3$ are as defined above.

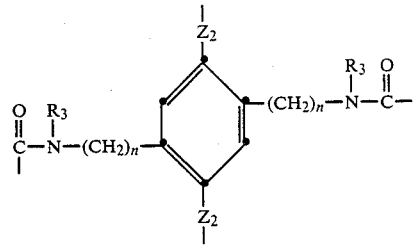

where n is 0 or 1 and $Z_2$, and $R_3$ are as defined above.

Such timing groups are described in, for example, U.S. Pat. No. 4,248,962.

III. Second Timing Group ($T_2$)

Examples of the second timing group ($T_2$) are represented by the following formulas:

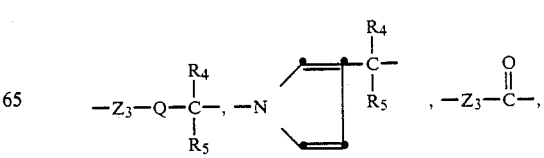

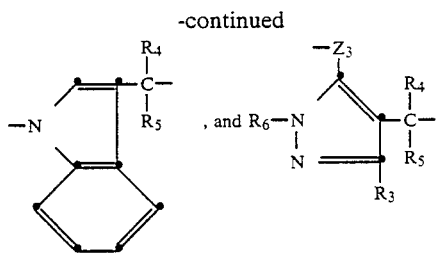

wherein the righthand bond is joined to PUG; the lefthand bond is attached to the first timing group ($T_1$), $Z_3$ is O, S or

$R_3$, $R_4$, $R_5$ and $R_6$ are individually a hydrogen atom, alkyl or aryl group, and Q is a pyridylene, 1,2- or 1,4-phenylene or naphthylene group. The pyridylene, phenylene or naphthylene can be unsubstituted or substituted by halogen, alkyl, alkoxy, —CN, —$NO_2$, —NHCOR or —COOR wherein R is alkyl.

Such timing groups are described in, for example, U.S Pat. No. 4,409,323 and *Research Disclosure*, December 1981, Item No. 21228.

IV. PUG's

A. PUG's which form development inhibitors upon release are described in such representative patents as U.S. Pat. Nos. 3,227,554; 3,384,657; 3,615,506; 3,617,291, 3,733,201 and U.K. Pat. No. 1,450,479. Preferred development inhibitors are iodide and heterocyclic compounds such as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzotriazoles and benzodiazoles. Structures of preferred development inhibitors moieties are:

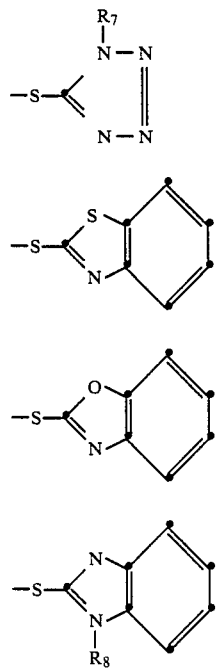

where $R_7$ and $R_8$ are individually hydrogen, alkyl of 1 to 8 carbon atoms (e.g. methyl, ethyl, butyl), phenyl or substituted phenyl and $R_9$ and $R_{10}$ are individually hydrogen or one or more halogen (e.g. chloro, fluoro, bromo), lower alkyl of 1 to 4 carbon atoms, carboxyl, carboxy esters, such as —$COOCH_3$, —$NHCOOCH_3$, —$SO_2OCH_3$, —$OCH_2CH_2SO_2CH_3$, —OCOCH$_2$CH$_3$ (C=O), —NHCCOCH$_3$ or nitro groups.

B. PUG's which are, or form, dyes upon release:

Suitable dyes and dye precursors include azo, azomethine, azopyrazolone, indoaniline, indophenyl, anthraquinone, triarylmethane, alizarin, nitro, quinoline, indigoid and phthalocyanine dyes or precursors of such dyes such as leuco dyes, tetrazolium salts or shifted dyes. These dyes can be metal complexed or metal complexable. Representative patents describing such dyes are U.S. Pat. Nos. 3,880,658; 3,931,144; 3,932,380; 3,932,381; and 3,942,987. Preferred dyes and dye precursors are azo, azomethine and indoaniline dyes and dye precursors. Structures of some preferred dyes and dye precursors are:

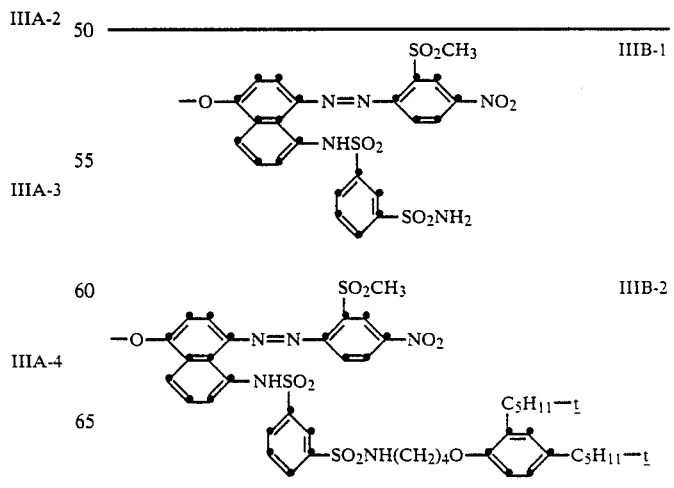

-continued

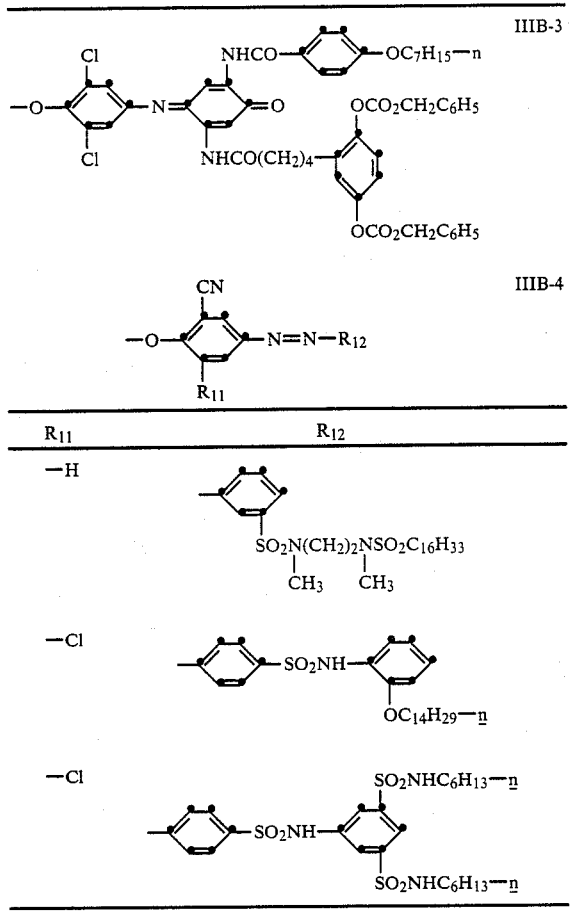

C. PUG's which are couplers:

Couplers released can be nondiffusible color-forming couplers, non-color forming couplers or diffusible competing couplers. Representative patents and publications describing competing couplers are: "On the Chemistry of White Couplers," by W. Püschel, Agfa-Gevaert AG Mitteilungen and der Forschungs-Laboratorium der Agfa-Gevaert AG, Springer Verlag, 1954, pp. 352–367; U.S. Pat. Nos. 2,998,314, 2,808,329, 2,689,793; 2,742,832; German Pat. No. 1,168,769 and British Pat. No. 907,274. Structures of preferred competing couplers are:

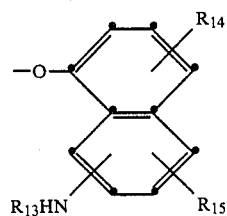

IIIC-1 where $R_{13}$ is hydrogen or alkylcarbonyl, such as acetyl, and $R_{14}$ and $R_{15}$ are individually hydrogen or a solubilizing group, such as sulfo, aminosulfonyl, and carboxy

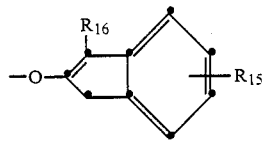

IIIC-2 where $R_{15}$ is as defined above and $R_{16}$ is halogen, aryloxy, arylthio, or a development inhibitor, such as a mercaptotetrazole, such as phenylmercaptetrazole or ethyl mercaptotetrazole.

D. PUG's which form developing agents:

Developing agents released can be color developing agents, black-and-white developing agents or cross-oxidizing developing agents. They include aminophenols, phenylene diamines, hydroquinones and pyrazolidones. Representative patents are: U.S. Pat. Nos. 2,193,015; 2,108,243; 2,592,364; 3,656,950; 3,658,525; 2,751,297; 2,289,367; 2,772,282; 2,743,279; 2,753,256; and 2,304,953.

Structures of preferred developing agents are:

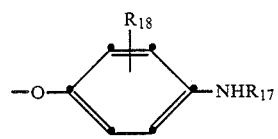

IIID-1 where $R_{17}$ is hydrogen or alkyl of 1 to 4 carbon atoms and $R_{18}$ is hydrogen or one or more halogen (e.g. chloro, bromo) or alkyl of 1 to 4 carbon atoms (e.g. methyl, ethyl, butyl) groups.

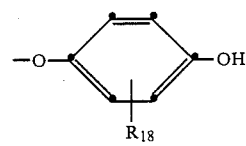

IIID-2 where $R_{18}$ is as defined above.

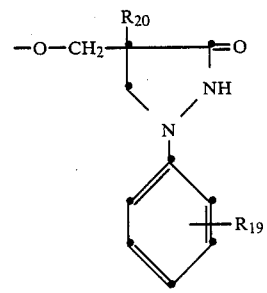

IIID-3

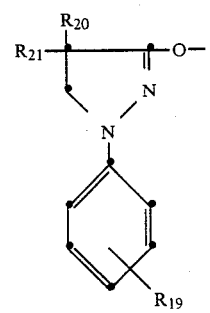

IIID-4

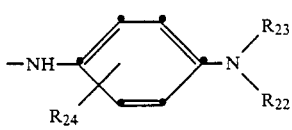 IIID-5

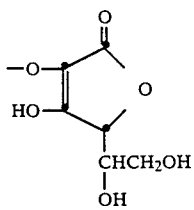 IIID-6 where $R_{19}$ is hydrogen or alkyl of 1 to 4 carbon atoms and $R_{20}$, $R_{21}$, $R_{22}$, $R_{23}$ and $R_{24}$ are individually hydrogen, alkyl of 1 to 4 carbon atoms (e.g. methyl, ethyl) lower hydroxyalkyl of 1 to 4 carbon atoms (e.g. hydroxymethyl) or lower sulfoalkyl.

E. PUG's which are bleach inhibitors:

Representative patents are U.S. Pat. Nos. 3,705,801; 3,715,208; and German OLS No. 2,405,279. Structures of preferred bleach inhibitors are:

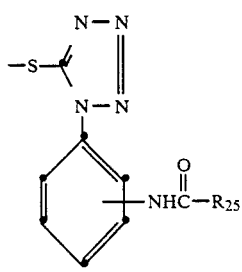 IIIE-1

IIIE-2

IIIE-3

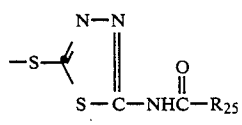 IIIE-4

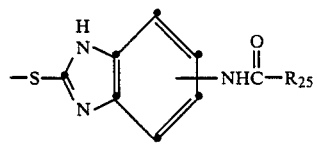

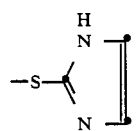

where $R_{25}$ is an alkyl group of 6 to 20 carbon atoms.

F. PUG's which are bleach accelerators:

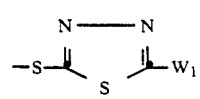 IIIF-1

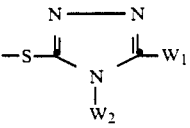 IIIF-2

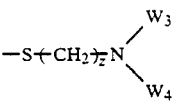 IIIF-3

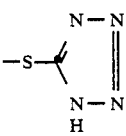 IIIF-4

—SCH$_2$CH$_2$COOH   IIIF-5 wherein $W_1$ is hydrogen, alkyl, such as ethyl and butyl, alkoxy, such as ethoxy and butoxy, or alkylthio, such as ethylthio and butylthio, for example containing 1 to 6 carbon atoms, and which may be unsubstituted or substituted; $W_2$ is hydrogen, alkyl or aryl, such as phenyl; $W_3$ and $W_4$ are individually alkyl, such as alkyl containing 1 to 6 carbon atoms, for example ethyl and butyl; z is 1 to 6.

The timing groups ($T_1$ and $T_2$) and PUG are selected and prepared to adjust to the activity of the adjoining carrier moiety, particularly a coupler moiety and the other groups of the coupler in order to optimize release of the PUG for its intended purpose. Accordingly, PUG groups of differing structural types are useful which enable timing groups having a range of activities. Various properties, such as pKa, are also usefully considered in optimizing the selection of optimum groups for a particular purpose. An example of such a selection could involve, for instance, a benzotriazole moiety as a PUG. Such a benzotriazole moiety can be released too slowly for some intended purposes from a timing group which involves a quinone-methide release mechanism and yet too quickly from a timing group which involves an intramolecular nucleophilic displacement mechanism; however, the benzotriazole moiety can be modified from

to

in order to modify the rate at which the benzotriazole moiety is cleaved from the timing group ($T_2$). Another illustration of modifying the PUG involves changing, for example, a mercaptotetrazole moiety from

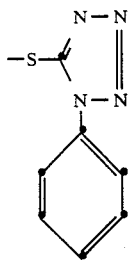

to

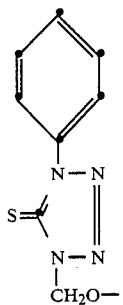

at elevated pH, such as above about pH 10, wherein the —CH₂O— portion of the group hydrolyzes rapidly leaving the remainder of the PUG free for its intended purpose.

A preferred compound A is a coupler represented by the formula:

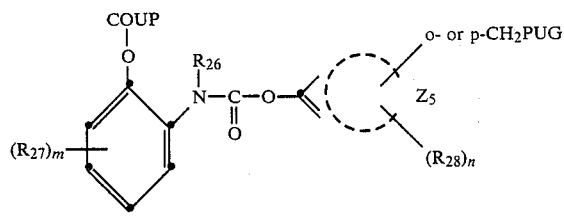

wherein:

$R_{26}$ is substituted or unsubstituted alkyl, such as substituted or unsubstituted alkyl containing 1 to 20 carbon atoms, for example methyl, ethyl, propyl, butyl or eicosyl; substituted or unsubstituted aryl, such as substituted or unsubstituted aryl containing 6 to 20 carbon atoms, for example, phenyl, hydroxyphenyl, aryloxyphenyl, and alkoxyphenyl;

$R_{27}$ is hydrogen or a substituent which does not adversely affect timing of release of the other portions of the compound, such as alkyl, for example alkyl containing 1 to 12 carbon atoms, alkylsulfonyl, for example —SO₂C₁₂H₂₅, nitro, alkoxy, halogen, sulfonamido, sulfamoyl or cyano;

$R_{28}$ is hydrogen or a substituent that advantageously influences the timing of release of PUG, such as alkyl containing 1 to 5 carbon atoms, for example methyl or butyl, nitro, halogen, cyano or alkoxy containing 1 to 5 carbon atoms;

COUP is a coupler moiety substituted in the coupling position by the remainder of the coupler;

PUG is a photographically useful group;

m and n are individually 0, 1 or 2;

$Z_5$ represents the atoms necessary to complete a pyridine, pyrazole, benzene, or naphthalene nucleus.

The photographic couplers of this invention can be incorporated in photographic elements and/or in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements of this invention can be processed by conventional techniques in which color forming couplers and color developing agents are incorporated in seperate processing solutions or compositions or in the element.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element according to this invention can comprise a support having thereon a red-sensitive silver halide emulsion unit having associated therewith a cyan dye image providing material, a green-sensitive silver halide emulsion unit having associated therewith a magenta dye image providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The couplers of this invention can be incorporated in or associated with one or more layers or units of of the photographic element. If ‐(T₁)‐(T₂)‐PUG and/or ‐(T₂)‐PUG and/or PUG are diffusible moieties, the layer or unit affected by PUG can be controlled by incorporating appropriate locations in the element a scavenger layer which will confine the action of ‐(T₂)‐PUG and/or PUG to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

The photographic couplers can be used in photographic elements in the same way as photographic couplers which release PUGs have previously been used in photographic elements. However, because of the improved ability to control the release of the PUG, the couplers permit enhanced effects or more selective effects than heretofore were possible. In addition, the couplers can be employed in applications where conventional couplers have previously been employed and a separate component was employed to provide a PUG.

Depending upon the nature of the particular PUG, the couplers can be incorporated in a photographic element for different purposes and in different locations.

When the PUG released from the coupler is a development inhibitor, the coupler can be employed in a photographic element like couplers which release development inhibitors have been used in the photographic art. Couplers of this invention which release a development inhibitor can be contained in, or in reactive association with, one or more of the silver halide emulsion units in a color photographic element. If the silver halide emulsion unit is composed of more than one layer, one or more of such layers can contain the coupler of this invention. The layers can contain other photographic couplers conventionally used in the art. The coupling reaction using couplers of this invention can form dyes of the same color as the color forming coupler(s) in the layer or unit, it can form a dye of a different color, or it can result in a colorless or neutral reaction product. The range of operation between layers of the development inhibitor released from the coupler of this invention can be controlled by the use of scavenger layers, such as a layer of fine grain silver halide emulsion. Scavenger layers can be in various locations in an element containing couplers of this invention. They can be located between layers, between the layers and the support, or over all of the layers.

Couplers of this invention which release development inhibitors can enhance the effects heretofore obtained with DIR couplers since they can release a development inhibitor at a distance from the point at which oxidized color developing agent reacted with the coupler, in which case they can provide, for example, enhanced interlayer interimage effects. Thus, the couplers of this invention can be employed to provide a degree of control over the effects obtainable from DIR couplers which heretofore could not be attained.

Photographic couplers of this invention which release bleach inhibitors or bleach accelerators can be employed in the ways described in the photographic art to inhibit the bleaching of silver or accelerated bleaching in areas of a photographic element.

Photographic couplers of this invention which release a dye or dye precursors can be used in processes where the dye is allowed to diffuse to an integral or separate receiving layer to form a desired image. Alternatively, the dye can be retained in the location where it is released to augment the density of the dye formed from the coupler from which it is released or to modify or correct the hue of that dye or another dye. In another embodiment, the dye can be completely removed from the element and the dye which was not released from the coupler can be retained in the element as a color correcting mask.

Couplers of this invention can be employed to release another coupler and the PUG. If the released coupler is a dye-forming coupler it can react with oxidized developing agent in the same or an adjacent layer to form a dye of the same or a different color or hue as that obtained from the primary coupler. If the released coupler is a competing coupler it can react with oxidized color developing agent in the same or an adjacent layer to reduce dye density.

Photographic couplers of this invention in which the PUG is a developing agent can be used to release a developing agent which will compete with the color forming developing agent, and thus reduce dye density. Alternatively, the couplers can provide, in an imagewise manner, a developing agent which because of such considerations as activity would not desirably be introduced into the element in a uniform fashion.

In chemical systems requiring timed release of a moiety as described herein, the release mechanisms can be initiated by any means that initiates cleavage of the first timing group from the carrier moiety. Depending on the particular carrier compound, the particular timing groups, the desired end use of the active moiety, the release mechanism can, for example, be initiated by reaction of the carrier compound with radiation, enzymes, moisture, acid or base, and/or oxidized reducing agent.

Compounds according to the invention can be prepared by methods known in the organic compound synthesis art. Typically, the couplers of this invention are prepared by first attaching the $T_1$ and $T_2$ groups to the appropriate coupler moiety, or a derivative of the coupler moiety. The product is then reacted with an appropriate derivative of the PUG to form the desired coupler. Known reactions are employed to perform these steps. The following examples illustrate the way in which these steps can be performed using specific reactants and reactions.

The following compounds illustrate methods of preparing compounds according to the invention.

In these examples Cp is the coupler moiety:

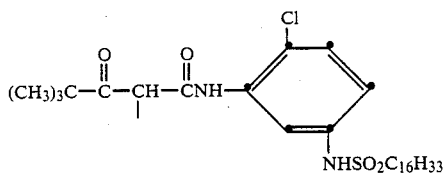

and the designation PMT means the moiety:

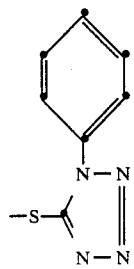

SYNTHESIS EXAMPLE A a. Preparation of Intermediate Compound A-1

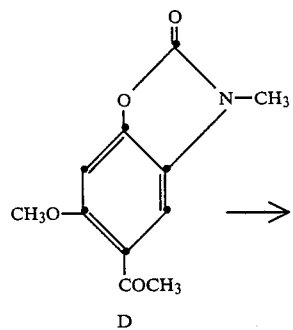
D

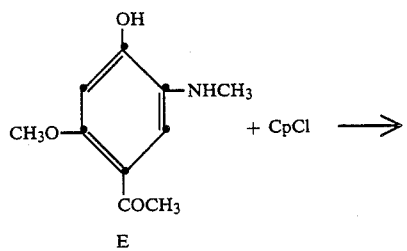
E

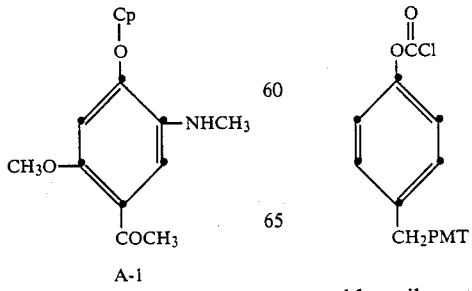
A-1

A slurry of 69 g (0.31 mol) of Compound D in a solution of 51.5 g (0.78 mol) potassium hydroxide in 300 ml water was heated to boiling for 15 minutes. Most of the solid dissolved. Addition of 7.5 g more potassium hydroxide in 50 ml water dissolved most of the remaining solid. The solution was filtered to remove some insoluble impurities. Careful hydrochloric acid treatment of the ice-cooled filtrate resulted in the evolution of carbon dioxide, and adjusting the pH to 6–7 with ammonium hydroxide gave a precipitate. After washing with water, then a 4:1 diethyl ether/ligroin mixture, 60.3 g of Compound E was obtained as a yellow-green solid.

A solution of 6.3 g (54 mmol) 1,1,3,3-tetramethylguanidine was added dropwise with stirring over 10 minutes to a solution of 16.2 g (27 mmol) α-chloro-α-pivalyl-2-chloro-5-(n-hexadecylsulfonamide)acetonilide (Cp-Cl) and 5.3 g (27 mmol) Compound E in 40 ml acetonitrile. After 1 hour the mixture was partitioned between ethyl acetate and 10% aqueous hydrochloric acid. The organic layer was washed with brine, dried, concentrated, and purified via silica gel chromatography to yield 18.3 g A-1 as a reddish-yellow oil with the expected nmr spectrum.

b. Preparation of Intermediate Compound B-1

To 50 ml acetyl chloride ice-cooled to 10° was added portionwise with stirring 5.1 g (40 mmol) p-hydroxybenzyl alcohol. After stirring overnight the mixture was concentrated, dissolved in methylene chloride, washed with 5% sodium bicarbonate, water, and dried over magnesium sulfate. The resulting p-acetoxybenzyl chloride in 50 ml methylene chloride was combined at room temperature with a solution of 8.2 g (41 mmol) 1-phenyl-1H-tetrazole-5-thiol sodium salt (NaPMT) in 50 ml water. Work-up and recrystallization in turn from toluene and from isopropanol yielded 7.0 g colorless crystals, m.p. 126°–8°, p-HOC₆H₄CH₂PMT. To an ice cold solution containing 5.0 g (21 mmol) of this phenolic product in 25 ml tetrahydrofuran and 2.5 g (21 mmol) N,N-dimethylaniline was added with stirring a 12% solution in toluene containing 4.1 g (41 mmol) phosgene. Work-up gave 7.25 g of Compound B-1 represented by the structure:

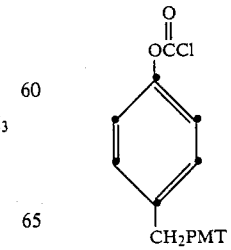

as a blue oil containing a trace of toluene.

c. Preparation of Compound 1 Represented by the Structure:

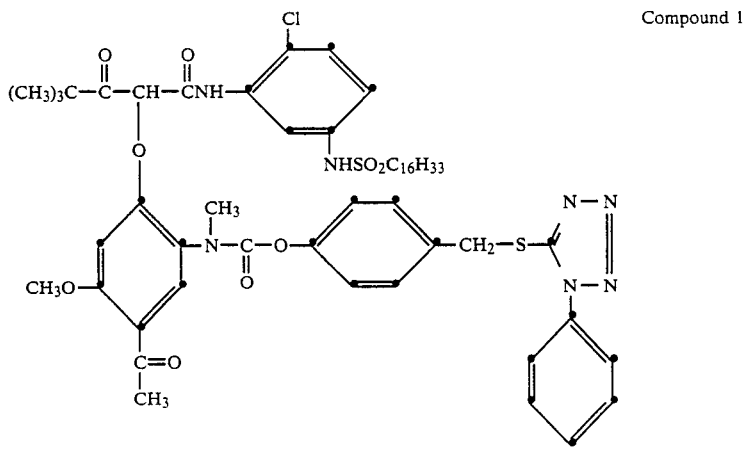

Compound 1

To a stirred solution of 6.0 g (8 mmol) A-1 in 20 ml tetrahydrofuran was added under nitrogen 0.97 g (8 mmol) N,N-dimethylaniline and 2.8 g (8 mmol) chloroformate ester B-1. After stirring one hour at room temperature, the reaction mixture was diluted with diethyl ether, washed in turn with saturated sodium chloride solution (brine), 10% aqueous hydrochloric acid, brine, then dried over magnesium sulfate and concentrated to 9.0 g of dark oil. Purification by silica gel chromatography gave 3.1 g light yellow glassy solid melting at 59 to 60° C., with the nmr, infrared, and mass spectra expected for compound 1.

SYNTHESIS EXAMPLE B

Preparation of Compound 2 Represented by the Structure:

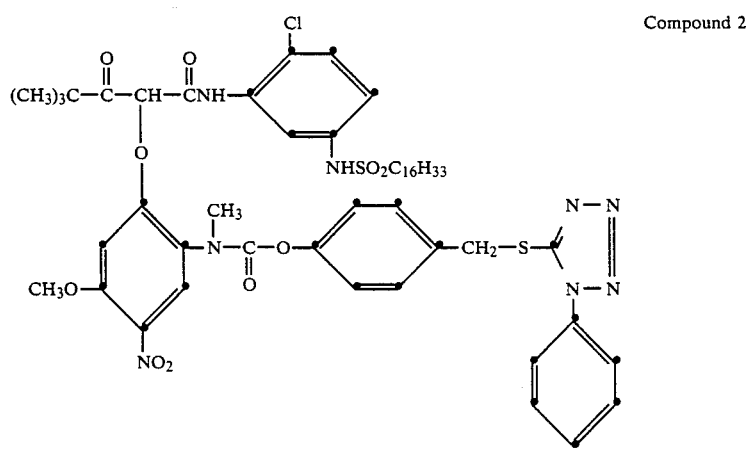

Compound 2

To a stirred solution of 8.3 g (11.0 mmol) A-2 represented by the structure:

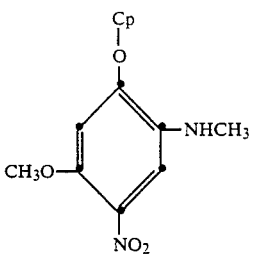

and 1.4 ml (11.0 mmol) N,N-dimethylaniline in 20 ml tetrahydrofuran was added under nitrogen a solution of 3.6 g (10.5 mmol) B-1. After one hour stirring the mixture was partitioned between diethyl ether and 10% aqueous hydrochloric acid. The organic layer was washed with 5% sodium carbonate solution, 5% aqueous hydrochloric acid, brine, then dried and concentrated to give 9.3 g of yellow oil. Purification by silica gel chromatography and washing with 5% aqueous sodium hydroxide yielded 3.4 g light yellow solid, m.p. 81°-2°, with the elemental analysis, infrared, nmr, and mass spectra expected for compound 2.

SYNTHESIS EXAMPLE C

Preparation of Compound 3 represented by the structure:

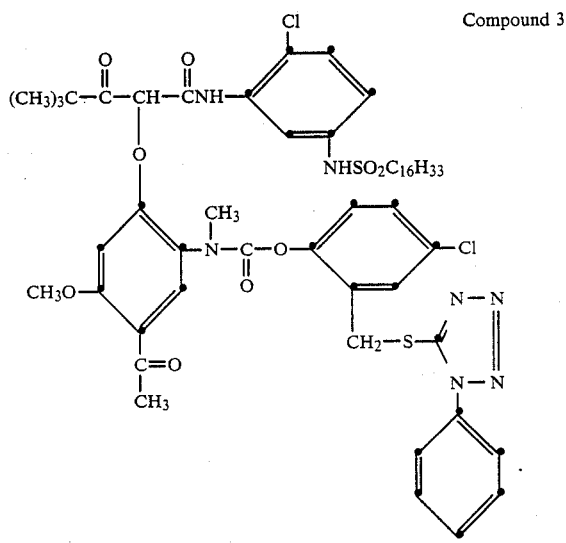

Compound 3

Using the procedure of Synthesis Example A, 9.0 g (12 mmol) of compound A-1 was combined with 5.4 g (14 mmol) of B-2 represented by the structure:

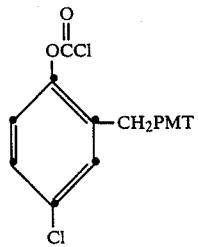

to give, after purification, 3.6 g white solid compound 3, m.p. 79°–80°, which was confirmed by elemental analysis and infrared spectra.

SYNTHESIS EXAMPLES D AND E

Similar combinations of A-3 represented by the structure:

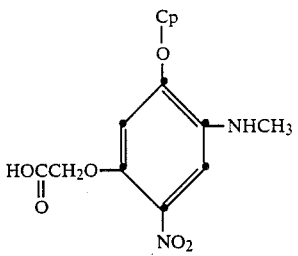

with B-2 and A-3 with B-1, according to the methods of Synthesis Examples A, B and C gave compounds 4 and 5, respectively, represented by the following structures:

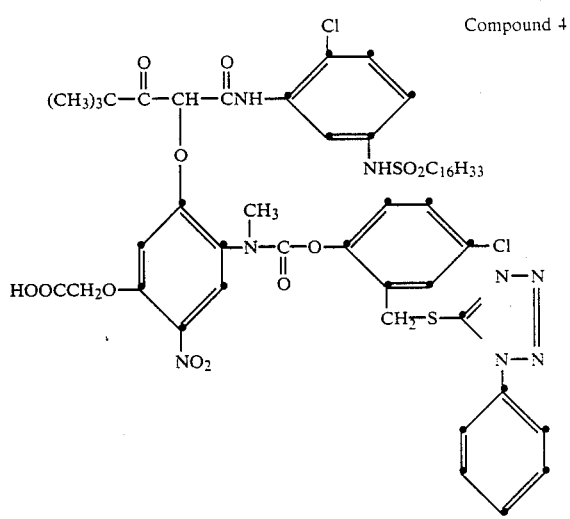

Compound 4

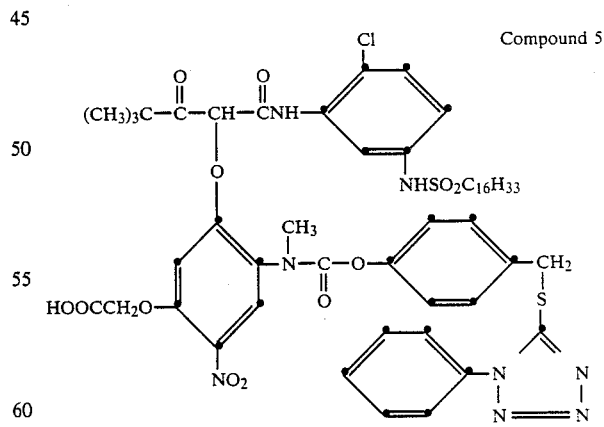

Compound 5

The following compounds 6 and 7 can also be prepared by methods like those described in Synthesis Examples A, B and C:

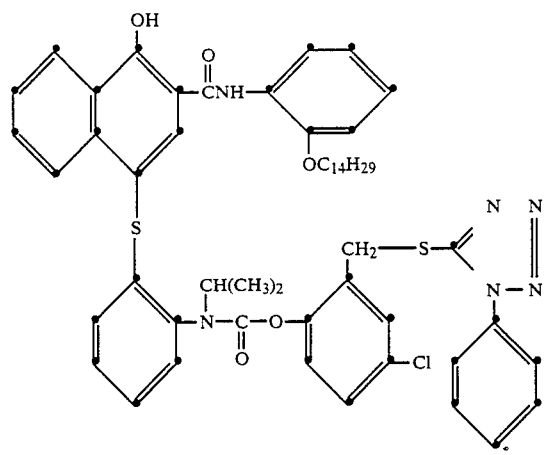
Compound 6
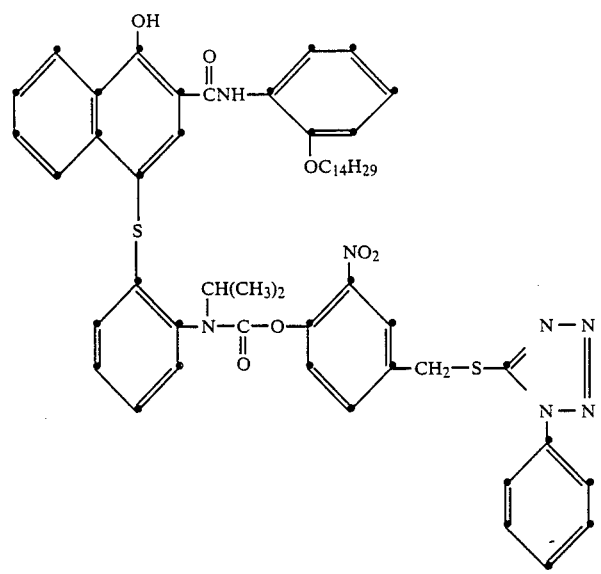
Compound 7
Other representative methods of synthesis are illustrated by the following structural reactions:
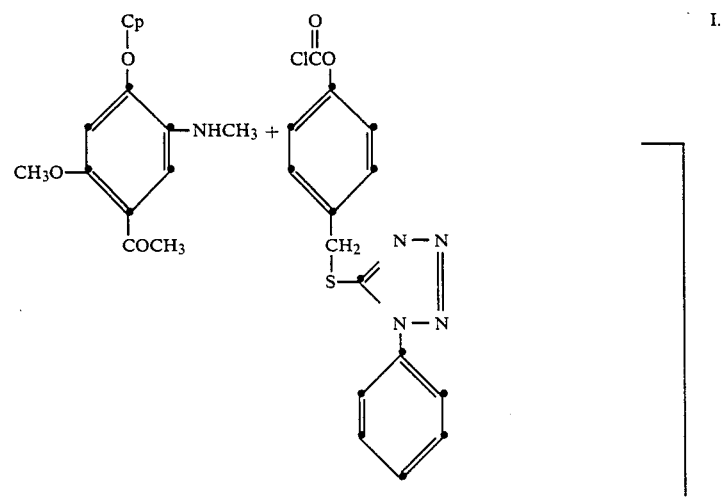
I.

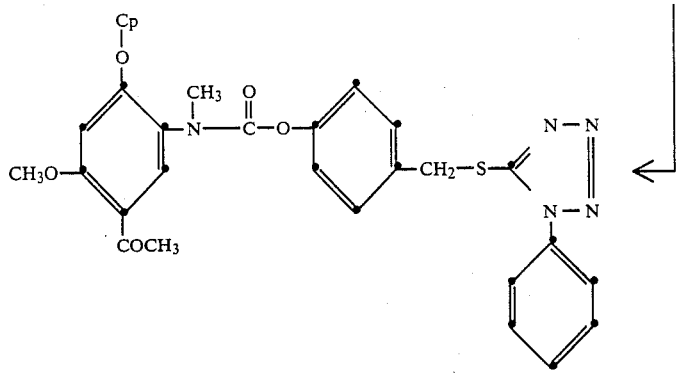

wherein Cp represents a coupler moiety.

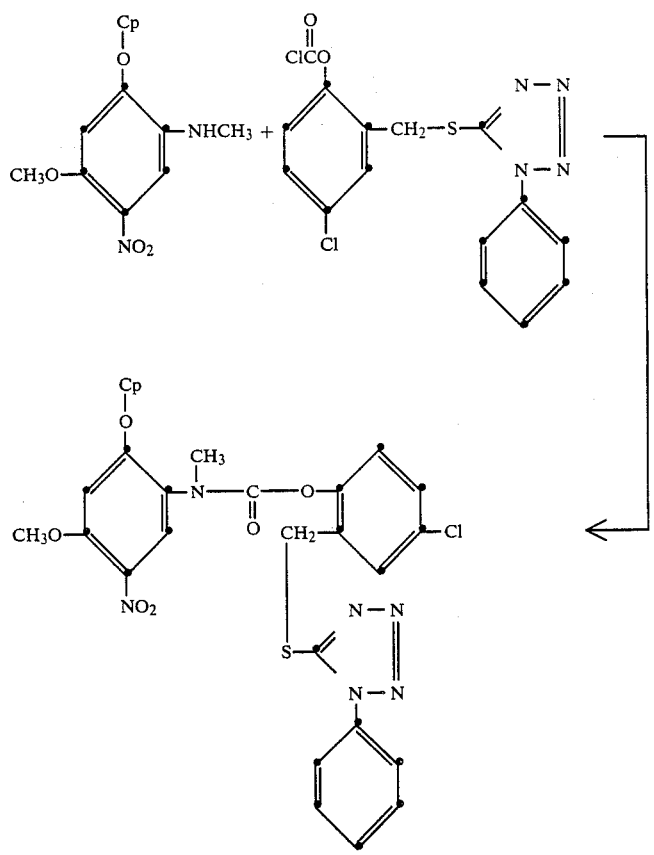

The following examples further illustrate the invention.

EXAMPLE 1

This illustrates the invention.

To demonstrate sharpness and interimage effects a photographic element format was employed in which a green-sensitive AgBrI "causer" gelatino emulsion layer provided a yellow image and an underlying red-sensitive AgBrI "receiver" gelatine emulsion layer provided a magenta image. The term causer gelatine emulsion herein means the layer from which a development inhibitor moiety is released. The term receiver gelatine emulsion layer herein means the layer upon which the development inhibitor acts. Interlayer interimage effects are described in, for example, Barr et al, *Photographic Science and Engineering*, Volume 13, No. 2, March–April, 1969, pages 78–80. Color photographic materials were prepared according to the following schematic layer structure (numerical values denote coating coverages in $mg/m^2$):

| | |
|---|---|
| Overcoat: | Gelatin - 2500; Gelatin hardener 1.75% to total gelatin |
| Causer Layer: | Green-sensitive AgBrI—1600; Gelatin-2400; Yellow dye-forming coupler and image modifying coupler (see Table 3) |
| Interlayer: | Antistain agent 2,5-Didodecylhydroquinone-115; Gelatin-620 |
| Receiver Layer: | Red-sensitive AgBrI—1600; Gelatin-2400; Magenta dye-forming coupler-650 |

| Film Support: | With antihalation gray silver-324; Gelatin-2452; Antistain agent-15 |
|---|---|

The hardener was bis(vinylsulfonylmethy)-ether and the silver bromoiodide (coating weight is that of silver) was a 6.4% iodide emulsion of 0.5μ average grain size chemically sensitized with sulfur and gold. The yellow dye-forming coupler was dispersed in half its weight of dibutyl phthalate, the magenta coupler in half its weight of tricresyl phosphate, and each image modifying coupler in twice its weight of diethyl lauramide. The yellow dye-forming coupler was either Coupler Y-1 or Y-2 as designated in Table 3:

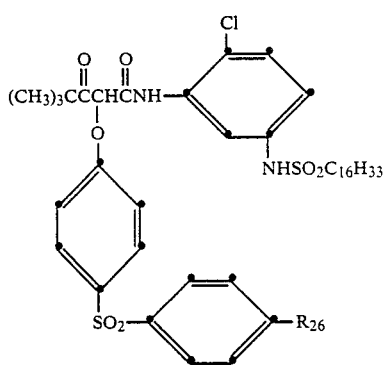

Y-1 $R_{26}$ = —OCH$_2$C$_6$H$_5$
Y-2 $R_{26}$ = —OH
The magenta dye-forming coupler was:

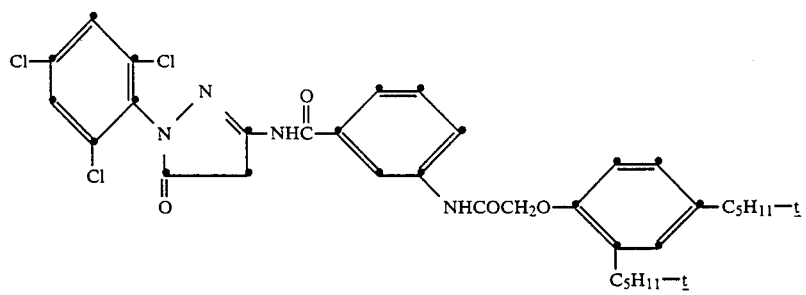

For interimage evaluation requiring image development in both the causer and receiving layers, the samples were exposed through a graduated-density test object and Wratten 12 (minus blue) filter. Wratten is a trademark of Eastman Kodak Co., U.S.A. For sharpness, evaluated by calculating CMT acutance values for 16 mm movie film (CMT-16) or 35 mm slide film (CMT-35)*, exposures were made through a Wratten 99 (green) filter. The materials were then processed at 38° C. as follows:

*This technique and the Cascaded Modulation Transfer (CMT) acutance are discussed in an article entitled: "An Improved Objective Method for Rating Picture Sharpness: CMT Acutance, " by R. G. Gendron, Journal of the SMPTE, 82, pages 1009-12 (December, 1973).

| | Time in Minutes |
|---|---|
| Color Developer | 2¾ |
| Stop (5% Acetic Acid) | 2 |
| Wash | 2 |
| Bleach (fe(CN)$_6$) | 2 |

| | Time in Minutes |
|---|---|
| Wash | 2 |
| Fix | 2 |
| Wash | 2 |

| Color developer composition | g/l |
|---|---|
| K$_2$SO$_3$ | 2.0 |
| 4-Amino-3-methyl-N—ethyl-N—β-hydroxyethylaniline sulfate | 3.35 |
| K$_2$CO$_3$ | 30.0 |
| KBr | 1.25 |
| KI | 0.0006 |
| Adjusted to pH 10 | |

The oxidized color developing agent generated by development of exposed silver halide couples with adjacent couplers to produce dye and release ─T$_1$─T$_2$─PMT from each image modifying coupler in the causer layer.

─T$_1$─T$_2$─PMT subsequently releases PMT. The effects of this inhibitor released from the modifier coupler can be measured by percent gamma repression in the causer (C) or receiver (R) layers.

$$C = 100 \frac{\gamma_o - \gamma}{\gamma_o} \text{ image of causer layer}$$

$$R = 100 \frac{\gamma_o - \gamma}{\gamma_o} \text{ image of receiver layer}$$

$\gamma_o$ = layer contrast without modifier $\gamma$ = layer contrast with modifier The C-R value indicates the relative inhibition effects occurring in the causer and receiver layers.

Similarly, the effect of inhibitor release when only the causer layer is exposed can be measured by percent density repression (% ΔD) in that layer.

$$\% \Delta D = 100 \frac{D_o - D}{D_o}$$

where D and $D_o$ are the net densities (image density minus fog density) for samples with and without incorporated modifier coupler, respectively.

Interimage Effects

In Table 3A comparison couplers are shown to give a wide range of interimage effects when both causer and receiver layers are exposed. All three (C-1, C-2, C-3) have a single timing group (T$_1$) releasing the inhibitor via formation of a 6-membered ring. Variation in the C-R value from +28 to −16 was controlled by attaching to the nitrogen atom either large hydrophobic or hydrophilic substituents, respectively. A small R substituent resulted in a C-R value closer to zero.

Comparison coupler C-1 herein is represented by the structure:

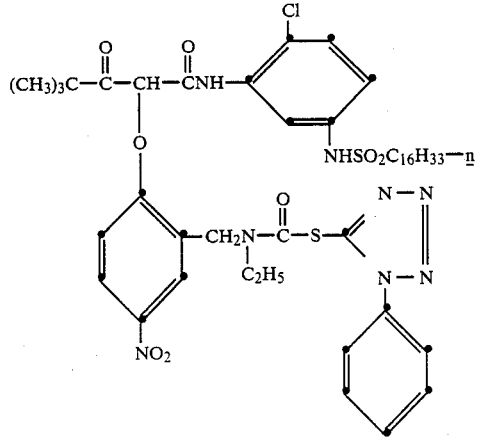

Comparison coupler C-2 herein is represented by the structure:

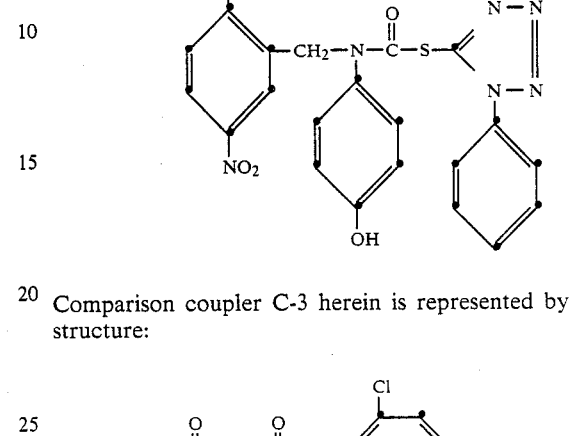

Comparison coupler C-3 herein is represented by the structure:

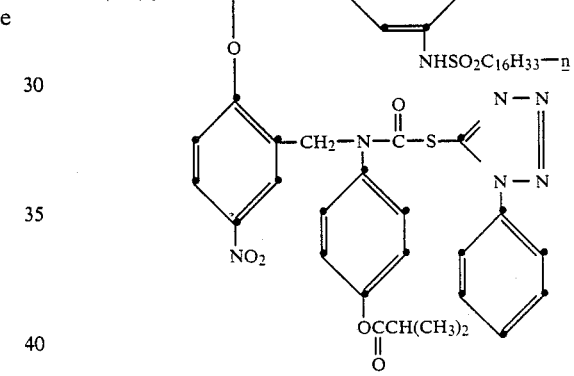

TABLE 3

| Example No. | Sample | Modifier (Coupler Level) | Interimage Effects | | | | | CMT-16 Sharpness** | | |
|---|---|---|---|---|---|---|---|---|---|---|
| | | | γC | γR | C | R | C-R | c | r | c-r |
| | A. Y-1 Image Coupler | | | | | | | | | |
| — | 1. None | (control) | 1.94 | 1.65 | — | — | — | 91.2 | 87.4 | 3.8 |
| 1 | 2. C-1 | (4.8) | 0.91 | 0.80 | 53 | 52 | 1 | 86.2 | 91.6 | 4.6 |
| 2 | 3. C-2 | (4.8) | 1.08 | 0.66 | 44 | 60 | −16 | 95.5 | 93.7 | 1.8 |
| 3 | 4. C-2 | (9.7) | 0.70 | 0.40 | 64 | 76 | −12 | 99.2 | 97.4 | 1.8 |
| 4 | 5. C-3 | (9.7) | 0.58 | 0.95 | 70 | 42 | 28 | 94.1 | 88.5 | 5.6 |
| 5 | 6. 2 | (9.7) | 0.87 | 0.85 | 55 | 49 | 6 | 96.3 | 91.0 | 5.3 |
| 6 | 7. 2 | (14.6) | 0.66 | 0.72 | 66 | 56 | 10 | 97.7 | 92.0 | 5.7 |
| 7 | 8. 3 | (14.5) | 1.32 | 1.13 | 32 | 32 | 0 | 93.1 | 87.7 | 5.4 |
| | B. Y-1 Image Coupler | | | | | | | | | |
| — | 9. None | (control) | 1.65 | 1.31 | — | — | — | 89.6 | 87.0 | 2.6 |
| 8 | 10. C-1 | (2.4) | 1.17 | 0.89 | 29 | 32 | −3 | 92.4 | 89.1 | 3.3 |
| 9 | 11. 1 | (8.5) | 1.04 | 0.84 | 37 | 36 | 1 | 91.7 | 89.0 | 3.7 |
| | C. Y-1 Image Coupler | | | | | | | | | |
| — | 12. None | (control) | 1.86 | 1.60 | — | — | — | 89.5 | 85.6 | 3.9 |
| 10 | 13. C-1 | (9.7) | 0.56 | 0.52 | 70 | 68 | 2 | 98.1 | 92.6 | 5.5 |
| 11 | 14. 4 | (14.6) | 0.69 | 0.54 | 63 | 66 | −3 | 99.7 | 95.6 | 4.1 |
| 12 | 15. 5 | (9.7) | 0.42 | 0.32 | 77 | 80 | −3 | 95.9 | 93.3 | 2.6 |
| 13 | 16. 5 | (14.6) | 0.31 | 0.26 | 83 | 84 | −1 | 101.2 | 98.2 | 3.0 |
| | D. Y-2 Image Coupler | | | | | | | | | |
| — | 17. None | (control) | 2.76 | 1.51 | — | — | — | 88.6 | 86.3 | 2.0 |
| 14 | 18. C-1 | (9.7) | 1.45 | 0.86 | 47 | 343 | −4 | 94.2 | 90.8 | 3.4 |
| 15 | 19. 4 | (14.6) | 1.38 | 0.69 | 50 | 54 | −4 | 94.3 | 91.5 | 2.8 |

TABLE 3-continued

| Example No. | Sample | Modifier (Coupler Level) | Interimage Effects | | | | | CMT-16 Sharpness** | | |
|---|---|---|---|---|---|---|---|---|---|---|
| | | | $\gamma C$ | $\gamma R$ | C | R | C-R | c | r | c-r |
| 16 | 20. 5 | (9.7) | 1.15 | 0.58 | 58 | 362 | −4 | 95.6 | 94.0 | 1.6 |

*Value in parenthesis is the image modifying coupler level as a mole percent of image coupler; Y-1 coated at 1291 mg (1.44 mmol)/m², Y-2 at 1076 mg (1.34 mmol)/m².
**Sharpness as CMT for the causer (c) or reciever (r) layer on 1./60 sec. neutral exposure.

Since coupling rates and $t_{\frac{1}{2}}$ values are each comparable among these couplers, the more negative C-R value may be interpreted as an enhanced tendency for the $T_1$-PMT fragment to diffuse farther before releasing inhibitor.

In contrast to the comparison couplers, the image modifying couplers of this invention have a first timing group ($T_1$) and a second timing group ($T_2$) in sequence. Attachment of hydrophilic groups such as —COOH in compounds 4 and 5 (see Tables 3C and D) provided more negative C-R values than for compounds 1 through 3, indicating a greater tendency for timely action on the receiver layer. However, these values varied over a smaller range, so that a balance of causer versus receiver effects closer to that of comparison coupler C-1 were achieved. It can be seen from Table 3 that image modifying couplers giving the greatest inhibition in a causer or receiver layer generally provided the greatest sharpness improvements in that layer. An unexpected 3 CMT improvement in receiver sharpness at comparable gamma was observed for sample 14 (invention Example 11) vs. sample 13 (comparison Example 10).

Sharpness

When only the causer layer was exposed and developed, the released inhibitor acted predominantly in that layer and provided greater sharpness than when the inhibition effects were spread between two layers. The data in following Table 4 show that image modifying coupler 5 of the invention when compared with comparison coupler C-1 at the same molar concentration (sample 20 vs. 18) provided unexpected improvements of 1 to 3 in CMT acutance, increasing in the higher density steps. A 50% higher molar concentration of coupler 4 (sample 19) also gave excellent sharpness but the largest improvements appeared in the lower density steps. Again a general correlation of sharpness was observed with the extent of inhibition, here measured as % ΔD.

TABLE 4

Causer Layer Sharpness

| Example No. | Sample No. | D* | % ΔD | CMT-16 | CMT-35 |
|---|---|---|---|---|---|
| | A. Step 1 | | | | |
| — | 17. Control | 0.97 | 0 | 90.4 | 98.6 |
| 17 | 18. Comparison Coupler | 0.57 | 41 | 93.2 | 99.9 |
| 18 | 19. Invention Coupler 4 | 0.49 | 49 | 96.0 | 102.2 |
| 19 | 20. Invention Coupler 5 | 0.45 | 54 | 94.5 | 101.1 |
| | B. Step 2 | | | | |
| — | 17. Control | 1.66 | 0 | 90.2 | 98.7 |
| 20 | 18. Comparison Coupler C-1 | 1.00 | 40 | 97.0 | 102.0 |
| 21 | 19. Invention Coupler 4 | 0.88 | 47 | 97.0 | 103.4 |
| 22 | 20. Invention Coupler 5 | 0.79 | 52 | 98.6 | 103.9 |
| | C. Step 3 | | | | |
| — | 17. Control | 1.87 | 0 | — | — |
| 23 | 18. Comparison Coupler C-1 | 1.36 | 27 | 97.6 | 102.5 |
| 24 | 19. Invention Coupler 4 | 1.26 | 33 | 98.7 | 104.4 |
| 25 | 20. Invention Coupler 5 | 1.11 | 41 | 100.5 | 105.6 |

*D = Density - Dmin of causer layer
Steps 1, 2, and 3 represent exposures increasing by 0.3 logE increments on film samples described in Table 3D.

Examples of other compounds according to the invention which can be prepared by methods as described and which are useful in photographic elements are as follows: (Examples 26 through 34 illustrate development inhibitor releasing couplers according to the invention.)

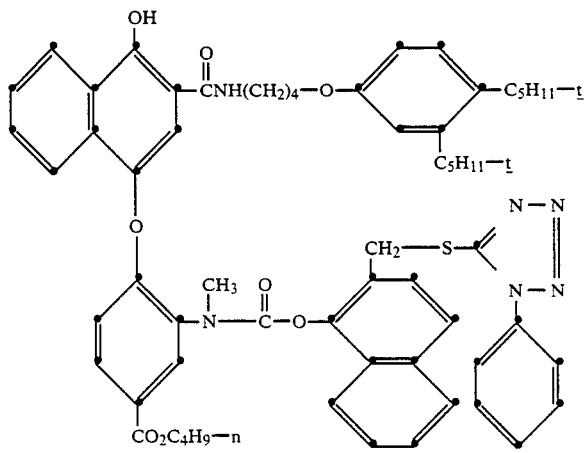

Example 26

-continued
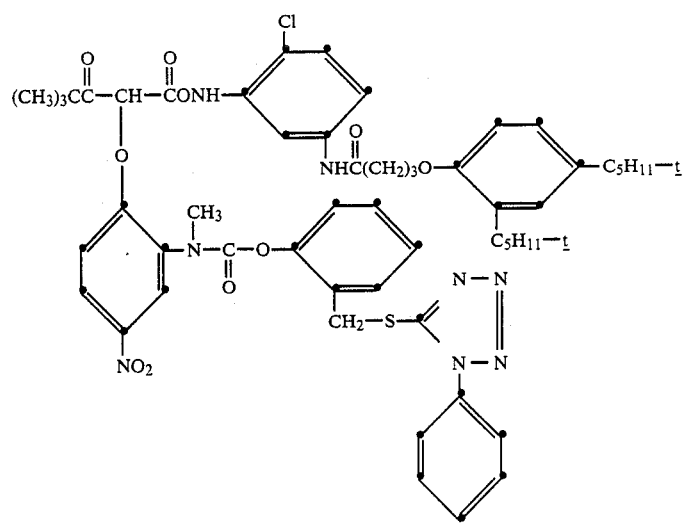
Example 27
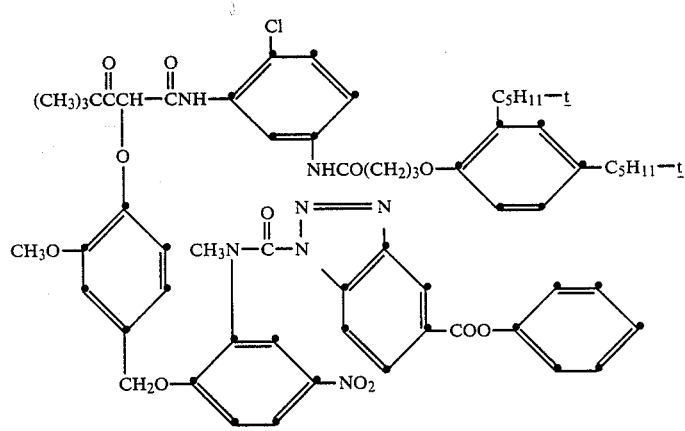
Example 28
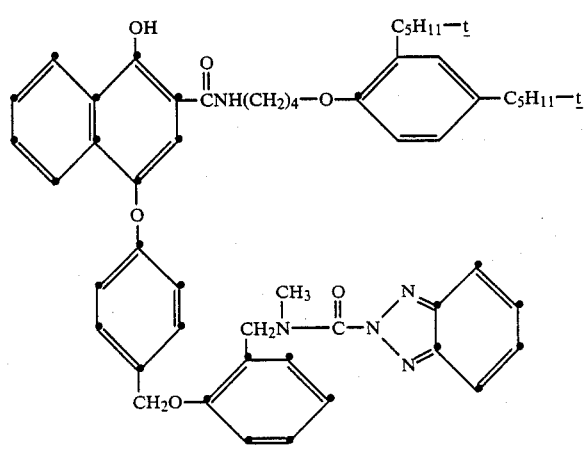
Example 29

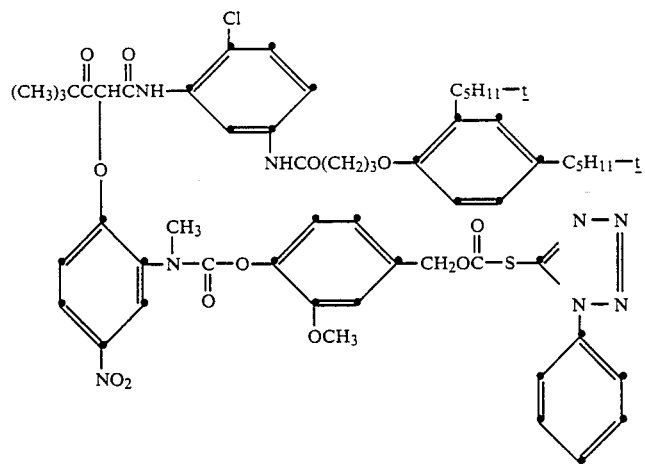
Example 30
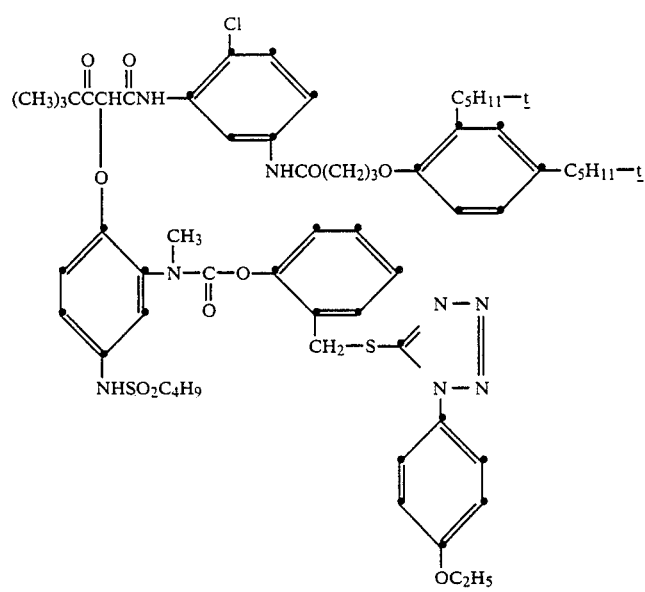
Example 31
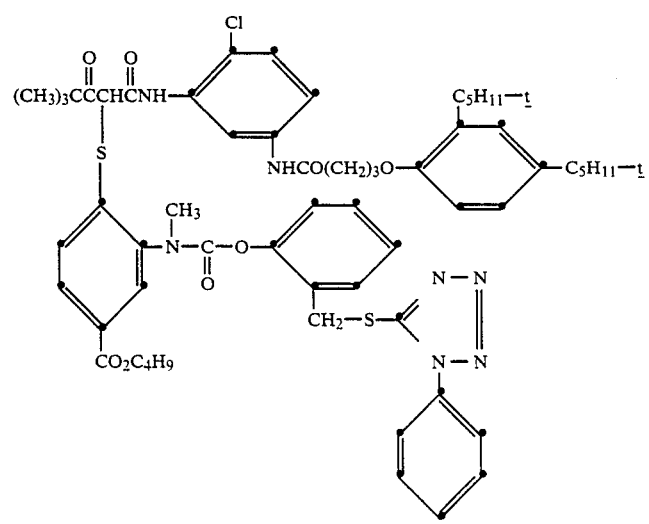
Example 32

Example 33
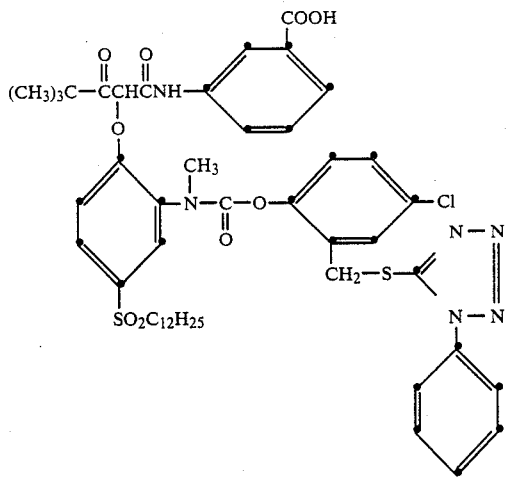
Example 34
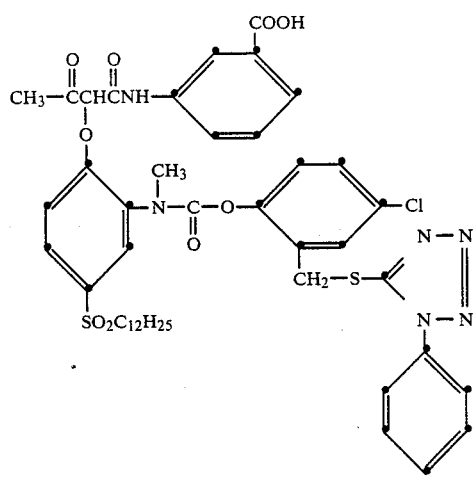
EXAMPLE 35
This illustrates a development accelerator releasing coupler according to the invention:
EXAMPLE 36
This illustrates an image stabilizer releasing coupler according to the invention:
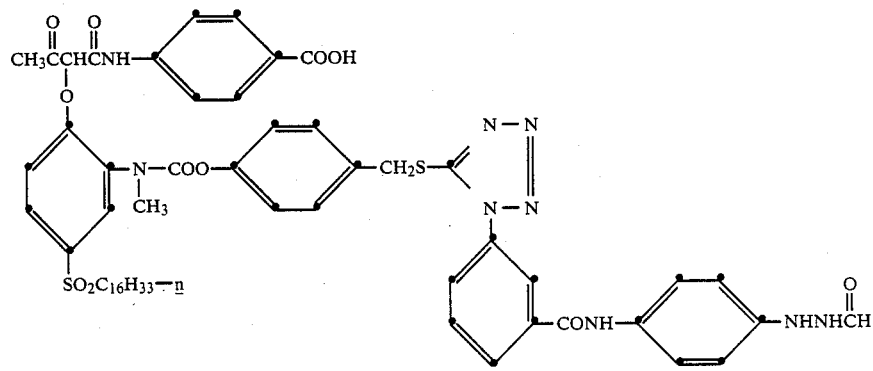

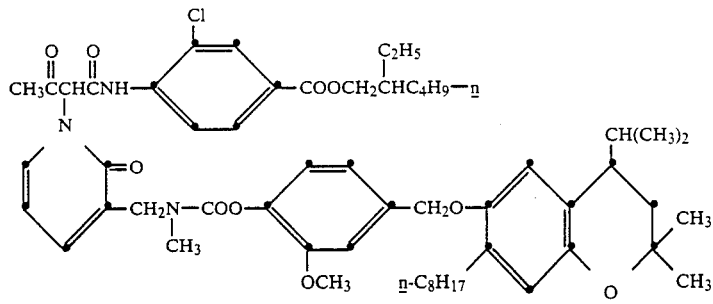

EXAMPLE 37

This illustrates a bleach inhibitor releasing coupler according to the invention:

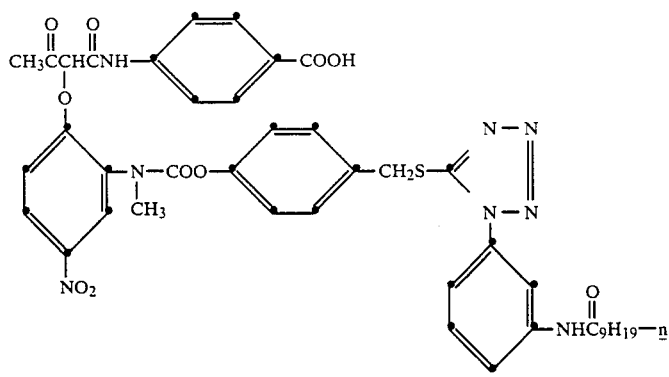

EXAMPLE 38

This illustrates a bleach accelerator releasing coupler according to the invention:

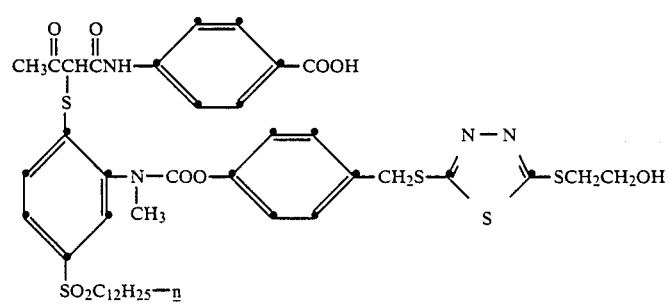

EXAMPLE 39

This illustrates a nucleator releasing coupler according to the invention:

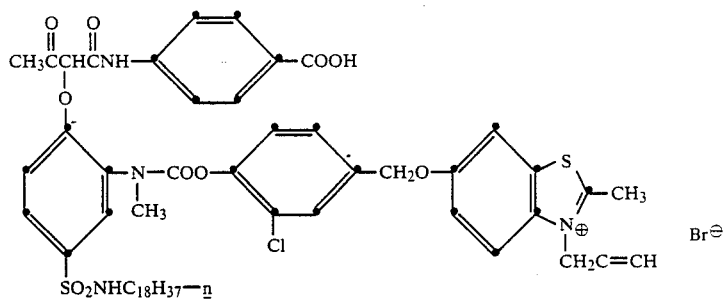

EXAMPLE 40

This illustrates a competing coupler releasing coupler according to the invention:

EXAMPLE 41
This illustrates an image coupler releasing coupler according to the invention:
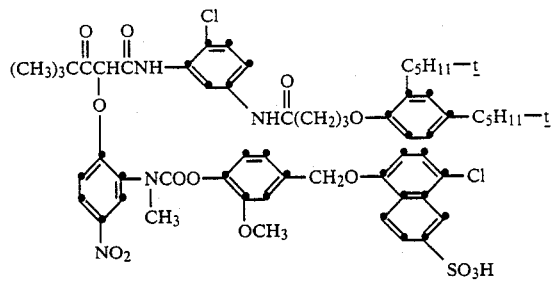
EXAMPLE 42
This illustrates a developing agent releasing coupler according to the invention:
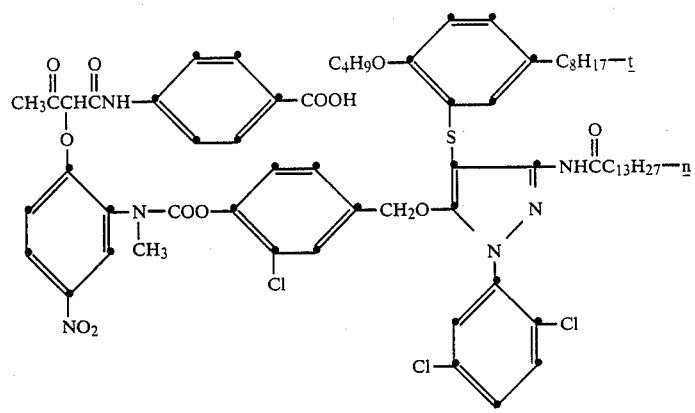
EXAMPLE 43
This illustrates a fixing agent releasing coupler according to the invention:
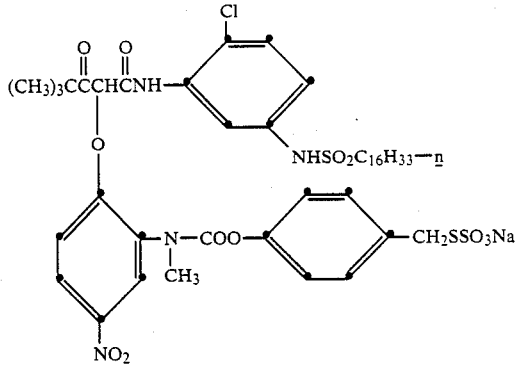
EXAMPLE 44
This illustraes a hardener releasing coupler according to the invention:
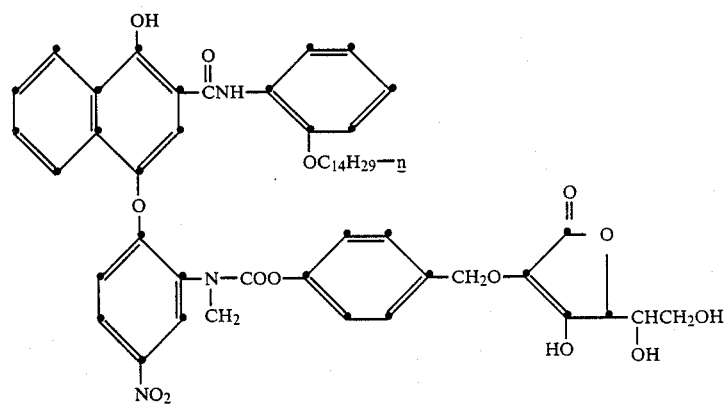

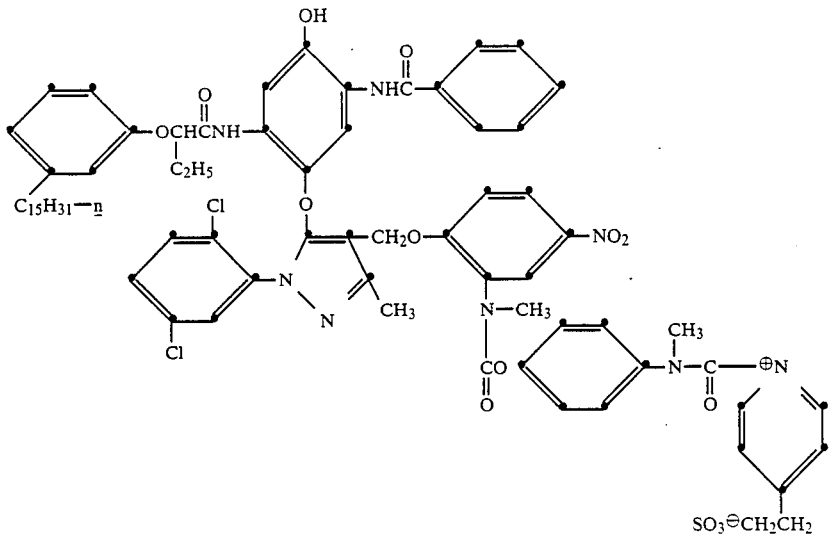
EXAMPLE 45
This illustrates a toner releasing coupler according to the invention:
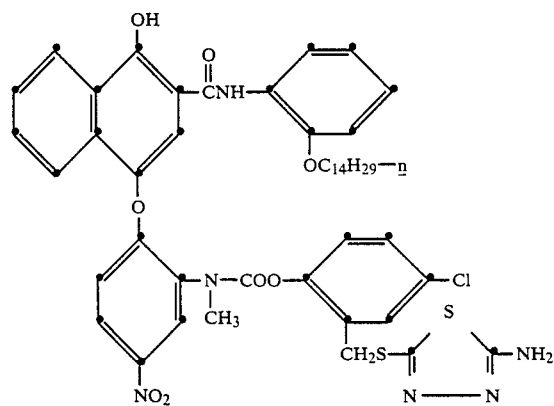
EXAMPLE 46
This illustrates an antifoggent releasing coupler according to the invention:
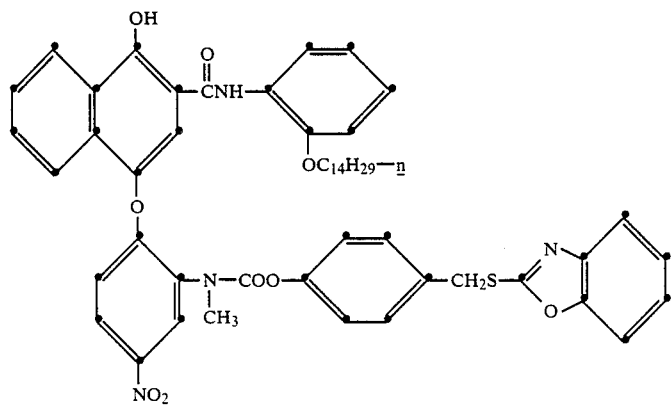
EXAMPLE 47
This illustrates a dye releasing coupler according to the invention:
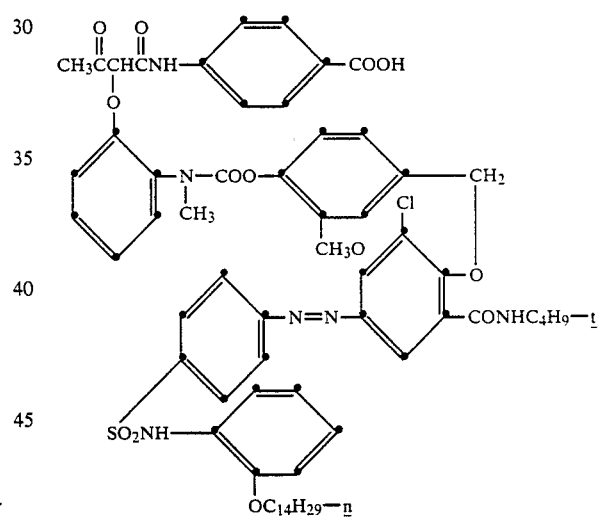

EXAMPLE 48

This illustrates an ultraviolet absorber releasing coupler according to the invention:

EXAMPLE 49

This illustrates a coupler according to the invention which has a first timing group capable of releasing a development accelerator and a second timing group that is capable of releasing a development inhibitor:

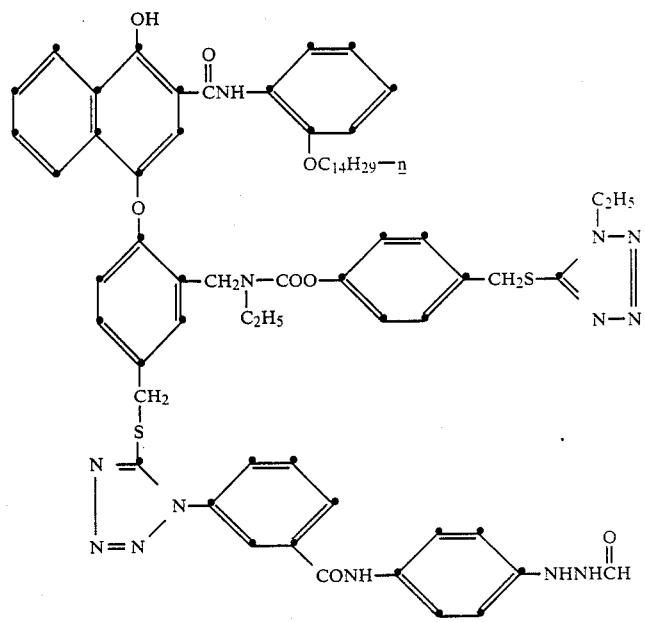

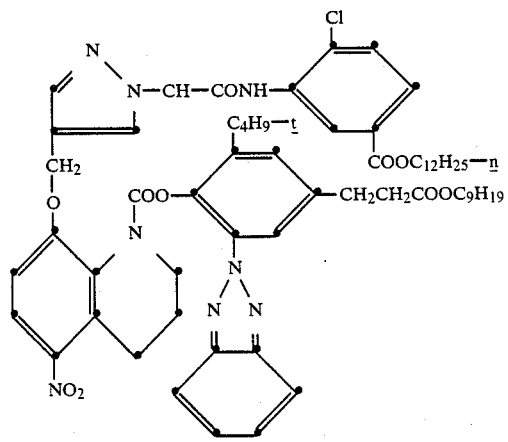

EXAMPLE 50

This illustrates a polymeric coupler according to the invention:

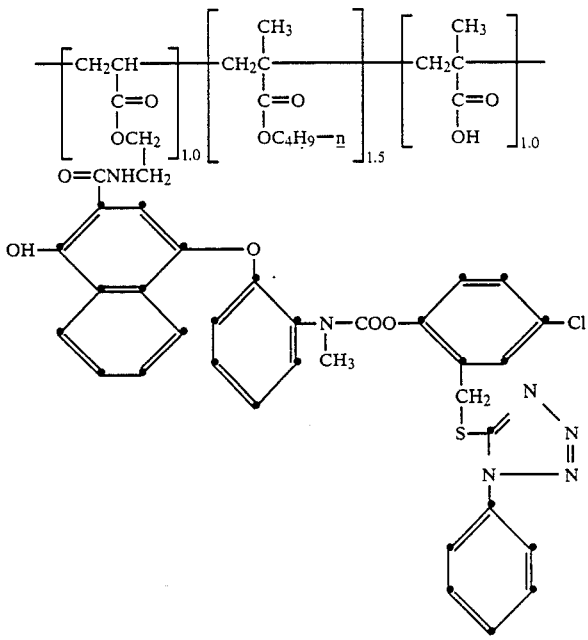

EXAMPLE 51

This illustrates a compound according to the invention which, in the presence of a reducing agent, is capable of releasing a development inhibitor:

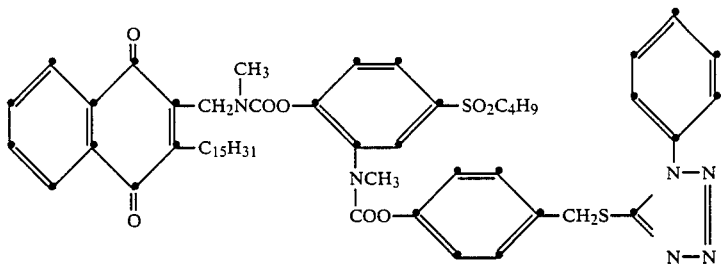

Another embodiment of the invention is a photographic element, as described, comprising a coupler represented by the formula:

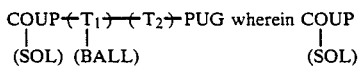

is a coupler moiety having a water solubilizing group (SOL) which enables the coupler moiety, upon release of the remainder of the coupler, to become a mobile moiety in the photographic element upon reaction with oxidized color developer;

is a first timing group having a ballast group (BALL) substituent which enables the coupler before processing to be immobile and then enables the first timing group to be immobile after reaction of the coupler with oxidized color developer;

BALL is a ballast group which enables the coupler before processing to be immobile and then during and after processing enables the first timing group to be immobile;

SOL is a water solubilizing group which enables the coupler moiety to be mobile after reaction of the coupler with oxidized color developing agent;

$T_2$ is a second timing group, different from the first timing group $T_1$; and PUG is a photographically useful group.

Upon exposure of the photographic element and processing, oxidized color developing agent reacts with the initially immobile coupler to form a mobile dye and an immobile first fragment

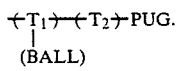

After a time delay, a second fragment which can be a mobile ─┤$T_2$├─PUG is released from immobile

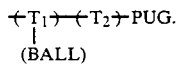

Finally after another time delay the PUG is released from ─┤$T_2$├─PUG. PUG can be mobile or mobile or immobile. In one embodiment, PUG is a development inhibitor. The coupler can serve, for example, as a development inhibitor releasing (DIR) coupler wherein the coupler upon processing leaves no residual dye in the imaging layer because the dye formed is water soluble and is removed from the imaging layer due to the water solubilizing group of the coupler moiety.

The sequential timed release of a useful compound from a carrier compound A according to the invention can also be useful in other applications wherein controlled timed release is desired. For example, the carrier compound can have a first timing group and a second timing group to release, for example, pharmaceutically useful moieties, including drugs; dyes; analytical agents; agricultural chemicals, such as fertilizers, pesticides and plant growth regulators.

The invention has been described in detail with particular reference to preferred embodiments thereof, but it will be understood that variations and modifications can be effected within the spirit and scope of the invention.

What is claimed is:

1. In a photographic element comprising a support, at least one photographic emulsion layer and at least one compound A capable upon reaction in a coupling position with an oxidized color developing agent of releasing a photographically useful group, the improvement
wherein the compound A comprises at least two differing timing groups in sequence capable, upon activation, of timing the release of the photographically useful group and
wherein two separate fragments are formed from the two differing timing groups upon processing the photographic element.

2. In a photographic element comprising a support, at least one photographic emulsion layer and at least one coupler capable upon reaction in a coupling position with an oxidized color developing agent of releasing a photographically useful group, the improvement wherein the coupler comprises at least two differing timing groups in sequence capable, upon activation, of timing the release of the photographically useful group and
wherein two separate fragments are formed from the two differing timing groups upon processing the photographic element.

3. A photographic element as in claim 1 or 2 wherein one of the two differing groups in sequence is a group capable of intramolecular nucleophilic displacement of the remaining portion of the compound A.

4. A photographic element as in claim 1 or 2 wherein one of the two differing groups in sequence is a group capable of a reaction in which an electron is transferred down a conjugated chain to release the remaining portion of the compound A.

5. A photographic element as in claim 1 or 2 wherein the photographically useful group is a releasable development inhibitor, developing agent, development accelerator, bleach inhibitor, bleach accelerator, dye, dye precursor, stabilizer, nucleator, fixing agent, image toner, hardener, antifoggant, or ultraviolet radiation absorber.

6. A photographic element as in claim 1 or 2 wherein the compound A or coupler yields a colorless product on reaction with oxidized color developing agent.

7. A photographic element as in claim 2 wherein the coupler is represented by the structure:

COUP-(T$_1$)-(T$_2$)-PUG wherein:
COUP is a coupler moiety;
T$_1$ is a first timing group capable of being released from COUP at the coupling position of COUP by reaction of COUP with oxidized color developer;
T$_2$ is a second timing group capable of being released from said first timing group after said first timing group is released from COUP; and,
PUG is a photographically useful group.

8. A photographic element comprising a support, at least one photographic silver halide emulsion layer and at least one coupler capable upon reaction with oxidized color developing agent of releasing a photographically useful group;
wherein the coupler comprises at least two differing timing groups, in sequence capable, upon activation, of timing the release of the photographically useful group;
wherein two separate fragments are formed from the two differing timing groups upon processing the photographic element; and
the coupler is represented by the formula:

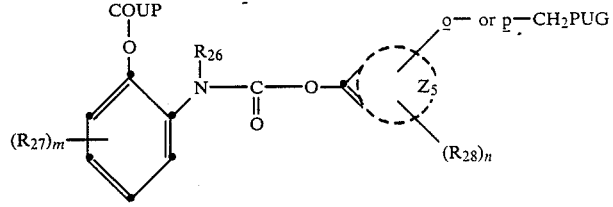

wherein:
R$_{26}$ is substituted or unsubstituted alkyl, or substituted or unsubstituted aryl;
R$_{27}$ is hydrogen or a substituent which does not adversely affect timing of release of the other portions of the photographic coupler;
R$_{28}$ is hydrogen or a substituent which advantageously influences the timing of release of PUG;
COUP is a coupler moiety substituted in the coupling position by the remainder of the coupler;
PUG is a photographically useful group;
m and n are individually 0 or 1;
Z$_5$ represents the atoms necessary to complete a carbocyclic or heterocyclic ring.

9. A photographic element as in claim 8 wherein the coupler is represented by the structure:

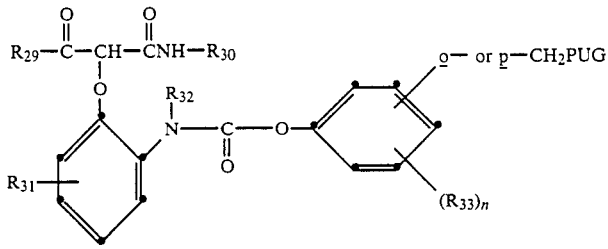

wherein:
R$_{29}$ is substituted or unsubstituted alkyl, substituted or unsubstituted aryl, or R$_{34}$NH;
R$_{30}$ is substituted or unsubstituted alkyl, or substituted or unsubstituted aryl;
R$_{31}$ is a hydrogen or a ballast group;
R$_{32}$ is alkyl;
R$_{33}$ is unsubstituted or substituted alkyl, chlorine, bromine, nitro, or alkoxy;
PUG is a photographically useful group; and
n is 0, 1 or 2.

10. A photographic element as in claim 8 wherein the coupler is represented by the formula:

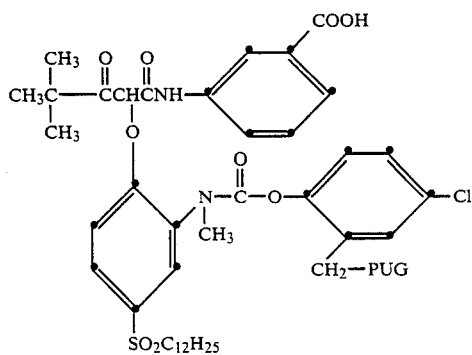

wherein PUG is a photographically useful group.

11. A process of forming a photographic image which comprises developing an exposed photographic silver halide emulsion layer with a color developing agent in the presence of a compound A capable of releasing a photographically useful group,
wherein the compound A comprises in a position that reacts with oxidized color developing agent at least two differing timing groups in sequence capable upon activation of timing the release of the photographically useful group and
wherein two separate fragments are formed from the two differing timing groups.

12. A process as in claim 11 wherein one of the two differing timing groups in sequence is a group capable of intramolecular nucleophilic displacement release of the remaining portion of the compound A.

13. A process as in claim 11 wherein one of the two differing groups in sequence is a group capable of a type reaction in which an electron is transferred down a conjugated chain to release the remaining portion of the compound A.

14. A process as in claim 11 wherein the compound A is a coupler represented by the formula:

COUP$-(T_1)-(T_2)-$PUG wherein:
COUP is a coupler moiety;
T$_1$ is a first timing group capable of being released from COUP at the coupling position of COUP by reaction of COUP with oxidized color developing agent;
T$_2$ is a second timing group capable of being released from said first timing group after said first timing group is released from COUP; and,
PUG is a photographically useful group.

15. A process of forming a photographic image which comprises developing an exposed photographic silver halide emulsion layer with a color developing agent in the presence of at least one coupler capable upon reaction with oxidized color developing agent of releasing a photographically useful group;
wherein the coupler comprises at least two differing timing groups, in sequence capable, upon activation, of timing the release of the photographically useful group;
wherein two separate fragments are formed from the two differing timing groups upon processing the photographic element; and,
the coupler is represented by the formula:

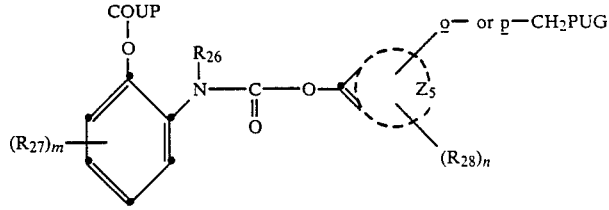

wherein:
R$_{26}$ is substituted or unsubstituted alkyl, or substituted or unsubstituted aryl;
R$_{27}$ is hydrogen or a substituent which does not adversely affect timing of release of the other portions of the photographic coupler;
R$_{28}$ is hydrogen or a substituent which advantageously influences the timing of release of PUG;

COUP is a coupler moiety substituted in the coupling position by the remainder of the coupler;

PUG is a photographically useful group;

m and n are individually 0 or 1;

$Z_5$ represents the atoms necessary to complete a carbocyclic or heterocyclic ring.

16. A process as in claim 15 wherein the compound A is a coupler represented by the formula:

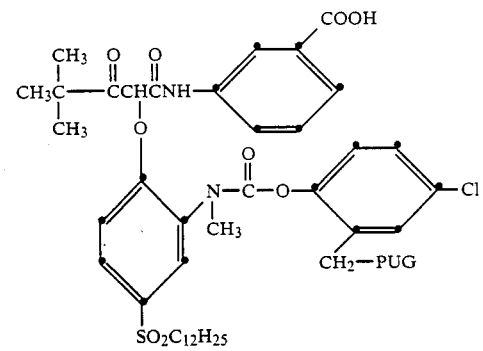

wherein PUG is a photographically useful group.

* * * * *